(12) United States Patent
Westman

(10) Patent No.: US 10,407,429 B2
(45) Date of Patent: Sep. 10, 2019

(54) PYRAZOLO[1,5-A]TRIAZIN-4-AMINE DERIVATIVES USEFUL IN THERAPY

(71) Applicant: Curovir AB, Kalmar (SE)

(72) Inventor: Jacob Westman, Järlåsa (SE)

(73) Assignee: Curovir AB, Kalmar (SE)

( * ) Notice: Subject to any disclaimer, the term of this patent is extended or adjusted under 35 U.S.C. 154(b) by 0 days.

(21) Appl. No.: 15/737,907

(22) PCT Filed: Jun. 10, 2016

(86) PCT No.: PCT/EP2016/063383
§ 371 (c)(1),
(2) Date: Dec. 19, 2017

(87) PCT Pub. No.: WO2016/206999
PCT Pub. Date: Dec. 29, 2016

(65) Prior Publication Data
US 2018/0298007 A1    Oct. 18, 2018

(30) Foreign Application Priority Data

Jun. 24, 2015   (EP) ................................. 15173687

(51) Int. Cl.
*C07D 487/04* (2006.01)
*A61P 31/14* (2006.01)
*A61K 31/53* (2006.01)

(52) U.S. Cl.
CPC ............ *C07D 487/04* (2013.01); *A61K 31/53* (2013.01); *A61P 31/14* (2018.01)

(58) Field of Classification Search
CPC .................................................... C07D 487/04
See application file for complete search history.

(56) References Cited

U.S. PATENT DOCUMENTS

| 6,191,131 B1 | 2/2001 | He et al. |
| 6,313,124 B1 | 11/2001 | He et al. |
| 2012/0184557 A1 | 7/2012 | Meijer et al. |

FOREIGN PATENT DOCUMENTS

| WO | 2001023387 A2 | 4/2001 |
| WO | 2010103486 A1 | 9/2010 |
| WO | 2013128029 A1 | 9/2013 |

OTHER PUBLICATIONS

International Search Report for corresponding International Application No. PCT/EP2016/063383 dated Jul. 21, 2016.
Written Opinion of the International Searching Authority for corresponding International Application No. PCT/EP2016/063383 dated Jul. 21, 2016.
Mejdrova et al., "Highly Selective Phosphatidylinositol 4-Kinase III-beta Inhibitors and Structural Insight into Their Mode of Action", Journal of Medicinal Chemistry, vol. 58, No. 9, May 14, 2015, pp. 3767-3793 (cited in specification on p. 1).
Gilligan et al., "8-(4-Methoxyphenyl)pyrazolo[1,5-a]-1,3,5-triazines: Selective and Centrally Active Corticotropin-Releasing Factor Receptor-1 (CRF)1) Antagonists", Journal of Medicinal Chemistry, vol. 52, No. 9, 2009, pp. 3073-3083 (cited in specification on p. 1).
Wagner et al., "A Selective Cannabinoid-1 Receptor Antagonist, PF-95453, Reduces Body Weight and Body Fat to a Greater Extent than Pair-Fed Controls in Obese Monkeys", The Journal of Pharmacology and Experimental Therapeutics, vol. 335, No. 1, 2010, pp. 103-113 (cited in specification on p. 1).
MacLeod et al., "Identification of a Series of Compounds with Potent Antiviral Activity for the Treatment of Enterovirus Infections", ACS Medicinal Chemistry Letters, vol. 4, 2013, pp. 585-589 (cited in specification on p. 1).
Van Der Schaar et al., "A Novel, Broad-Spectrum Inhibitor of Enterovirus Replication That Targets Host Cell Factor Phosphatidylinositol 4-Kinase IIIB", Antimicrobial Agents and Chemotherapy, vol. 57, No. 10, Oct. 2013, pp. 4971-4981 (cited in specification on p. 1).
Bianco et al., "Metabolism of Phosphatidylinositol 4-Kinase IIIa-Dependent PI4P Is Subverted by HCV and Is Targeted by a 4-Anilino Quinazoline with Antiviral Activity", PLos Pathogens, vol. 8, Issue 3, Mar. 2012, pp. 1-17 (cited in specification on p. 1).
Lamarche et al., "Anti-Hepatitis C Virus Activity and Toxicity of Type III Phosphatidylinositol-4-Kinase Beta Inhibitors", Antimicrobial Agents and Chemotherapy, vol. 56, No. 10, Oct. 2012, pp. 5149-5156 (cited in specification on p. 1).
Decor et al., "Design, synthesis and biological evaluation of novel aminothiazoles as antiviral compounds acting against human rhinovirus", Bioorganic & Medicinal Chemistry Letters, vol. 23, 2013, pp. 3841-3847 (cited in specification on p. 1).

(Continued)

*Primary Examiner* — Alexander R Pagano
*Assistant Examiner* — Ebenezer O Sackey
(74) *Attorney, Agent, or Firm* — Renner, Otto, Boiselle & Sklar, LLP

(57) ABSTRACT

A compound of formula (I), or a pharmaceutically acceptable salt thereof, useful in therapy, in particular in the treatment of a viral infection.

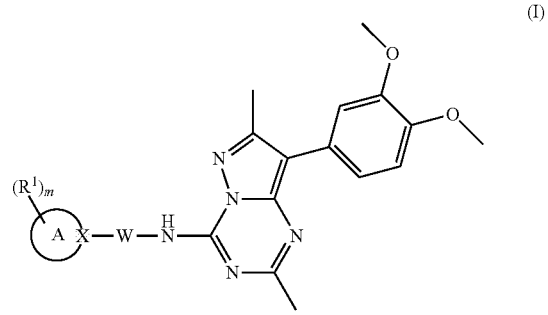

17 Claims, No Drawings

(56) References Cited

OTHER PUBLICATIONS

Long et al., "Synthesis toward CRHR1 Antagonists through 2,7-Dimethylpyrazolo[1-5-a][1,3,5]triazin-4(3H)-one C—H Arylation", The Journal of Organic Chemistry, vol. 80, 2015, pp. 4716-4721 (cited in specification on p. 1).

PYRAZOLO[1,5-A]TRIAZIN-4-AMINE DERIVATIVES USEFUL IN THERAPY

This application is a national phase of International Application No. PCT/EP2016/063383 filed Jun. 10, 2016 and published in the English language, which claims priority to European Application No. 15173687.3 filed Jun. 24, 2015.

FIELD OF THE INVENTION

The present invention relates generally to novel compounds having usefulness in therapy, in particular in the treatment of conditions caused by certain viruses, such as diabetes, cancer, neurodegenerative diseases such as Alzheimer's disease and amyotrophic lateral sclerosis.

More particularly the invention relates to pyrazolo[1,5-a] triazin-4-amine derivatives having a usefulness in therapy.

BACKGROUND OF THE INVENTION

Pyrazolo[1,5-a] triazin-4-amine is a scaffold previously used in medicinal chemistry and derivatives thereof are known for their potent utility as corticotropin-releasing factor receptor-1 (CRF1) antagonists which may be potential anxiolytic and antidepressant drugs (for example Gilligan et al (J. Med. Chem. 2009, 52, 3073-3083). Pexacerfont is a pyrazolo[1,5-a]triazin-4-amine drug developed by Bristol-Myers Squibb and acts as a CRF-1 antagonist which have been tested clinically. The scaffold has also been described as present in cyclin-dependent kinase inhibitors (WO2013128029), casein kinase inhibitors and DYRK1A kinase inhibitors (WO2010103486) useful for treatment of various diseases. The scaffold has further been described as present in cannabinoid 1 receptor antagonists (J. Pharm. Exp. Ther. (2010), 335(1), 103-113).

Similar scaffolds have been described as present in phosphatidylinositol 4-kinase (PI4K) inhibitors (McLeod et al (ACS Med. Chem. Lett. 2013, 4(7), 585-589) and van der Schaar et al (Antimicrobial Agents Chemother. 2013, 57(10), 4971-4981) and inhibitors of PI4K have shown to be potent antivirals (Bianco et al, PLoS Pathogens, 2012, 8(3), 1-17; LaMarche et al, Antimicr. Agents and Chemother. 2012, 56(10), 5149-5156; Décor et al, Bioorg Med Chem Lett. 2013, 23, 3841-7).

Pyrazolo[1,5-a] triazin-4-amine have been described as PI4K inhibitors with antiviral potency in Mejdrova et al (J. Med. Chem., 2015, 58 (9), pp 3767-3793).

There still remains a need for new therapeutically active compounds.

SUMMARY OF THE INVENTION

A first aspect is a compound of formula (I)

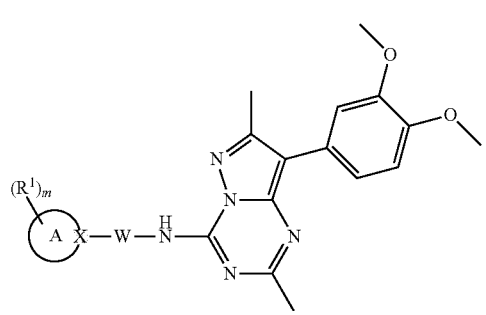

(I)

or a pharmaceutically acceptable salt thereof, wherein
W is $CH_2$ or $CH_2$—$CH_2$;
X is C or CH;
ring A is 5- or 6-membered carbocyclyl or 5- or 6-membered heterocyclyl;
m is an integer of from 0 to 3;
each $R^1$ is independently selected from C1-C6 alkyl optionally substituted by one or more halogen, $R^2O$, halogen, $R^3R^4NC(O)$, $R^5C(O)N(R^6)$, $R^7OC(O)$, $R^8C(O)O$, $R^9S(O)_2$, $R^{10}S(O)_2N(H)$, $R^{11}C(O)$, $R^{12}R^{13}N$, —O and $R^{14}R^{15}NS(O)_2$; and
when m is at least 2, two $R^1$ attached to adjacent atoms of ring A may form, together with the atoms to which they are attached, a 5- or 6-membered heterocyclic or carbocyclic ring;
each $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from H and C1-C6 alkyl, wherein any alkyl is optionally substituted by one or more halogen;
$R^{15}$ is selected from H, C1-C6 alkyl, $R^{16}C(O)$, $R^{17}OC(O)$, and $R^{18}R^{19}NC(O)$; and
each $R^{16}$, $R^{17}$, $R^{18}$, and $R^{19}$ is independently selected from H and C1-C6 alkyl, wherein any alkyl is optionally substituted by one or more halogen.

In some embodiments of a compound of formula (I), W is $CH_2$, X is C, and ring A is phenyl or 5- or 6-membered heteroaryl; e.g. W is $CH_2$, X is C, and ring A is phenyl; or W is $CH_2$, X is C, and ring A is 5- or 6-membered heteroaryl; or W is $CH_2$, X is C, and ring A is 6-membered heteroaryl; or W is $CH_2$, X is C, and ring A is 5-membered heteroaryl.

A further aspect is a compound of formula (I), or a pharmaceutically acceptable salt thereof, for use as an inhibitor of phosphatidylinositol 4-kinase IIIβ.

A further aspect is a compound of formula (I), or a pharmaceutically acceptable salt thereof, for use in therapy.

A still further aspect is a pharmaceutical composition comprising a compound of formula (I), or a pharmaceutically acceptable salt thereof, and optionally a pharmaceutically acceptable excipient.

A further aspect is a compound of formula (I), or a pharmaceutically acceptable salt thereof, for use in the treatment of a viral infection. In some embodiments, the viral infection is a non-enveloped single-stranded (+) RNA viral infection.

Still a further aspect is a compound of formula (I), or a pharmaceutically acceptable salt thereof, for use in the treatment of a neurodegenerative disease such as multiple sclerosis, Parkinson's disease, amyotrophic lateral sclerosis, Alzheimer's disease, Huntington's disease, poliomyelitis, encephalitis, meningitis, sepsis, cancer, paralysis, myocarditis, diabetes, common cold, hand-foot-and-mouth disease, herpangina, pleurodynia, diarrhea, mucocutaneous lesions, respiratory illness, conjunctivitis, myositis, and chronic fatigue syndrome.

The use of the compound of formula (I) or the pharmaceutically acceptable salt thereof for the preparation of a pharmaceutical composition for the treatment of a disorder as mentioned herein above also is provided, as well as a method for the treatment of a disorder as mentioned herein above by administration of a therapeutically effective amount of a compound of formula (I) or a pharmaceutically acceptable salt thereof to a mammal in need thereof.

DETAILED DESCRIPTION OF THE INVENTION

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Unless otherwise stated or indicated, the term "C1-6 alkyl" denotes a straight or branched alkyl group having from 1 to 6 carbon atoms. Examples of said C1-6 alkyl include methyl, ethyl, n-propyl, iso-propyl, n-butyl, iso-butyl, sec-butyl, t-butyl and straight- and branched-chain pentyl and hexyl.

Unless otherwise stated or indicated, the term "halogen" (or "halo") refers to fluorine (F), chlorine (Cl), or bromine (Br).

A moiety of the type RR'NC(O) is a moiety of formula

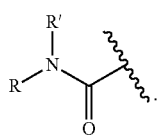

A moiety of the type RC(O)N(R') is a moiety of formula

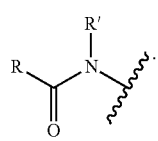

A moiety of the type ROC(O) is a moiety of formula

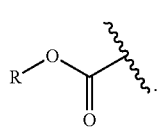

A moiety of the type RC(O)O is a moiety of formula

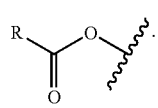

A moiety of the type RS(O)$_2$ is a moiety of formula

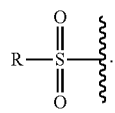

A moiety of the type RS(O)$_2$N(H) is a moiety of formula

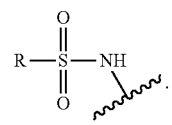

A moiety of the type RR'NS(O)$_2$ is a moiety of formula

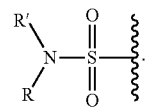

A moiety of the type RC(O) is a moiety of formula

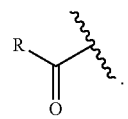

A moiety of the type RR'N is a moiety of formula

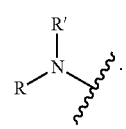

As used herein, the term "carbocyclyl" or "carbocyclic ring" refers to a saturated or unsaturated (e.g. monounsaturated or diunsaturated), non-aromatic or aromatic cyclic moiety containing only carbon atoms in the ring.

Examples of non-aromatic carbocylyl are pentyl, hexyl or hexenyl, while phenyl is an example of aromatic carbocyclyl.

The term "heterocyclyl" (or "heterocyclic ring") refers to a saturated or unsaturated, aromatic or non-aromatic cyclic moiety containing not only carbon atoms, but also at least one other atom in the ring, e.g. selected from nitrogen (N), sulphur (S) and oxygen (O), in particular N and O.

When non-aromatic, the heterocyclyl e.g. may be piperidinyl, or 1,2,3,4-tetrahydropyridinyl. Other examples of non-aromatic heterocyclyl include morpholinyl, pyrrolidinyl, piperazinyl, tetrahydrothienyl, and tetrahydrofuryl.

When aromatic, the heterocyclyl also may be referred to as "heteroaryl", which refers to an aromatic ring containing at least one ring heteroatom, such as furyl, isoxazolyl, isothiazolyl, imidazolyl, pyridyl, pyrrolyl, pyrazolyl, pyrimidinyl, pyridazinyl, pyrazinyl, oxadiazolyl, oxazolyl, thienyl, thiadiazolyl, thiazolyl, triazolyl, and tetrazolyl.

The term "aromatic", as used herein, refers to an unsaturated cyclic moiety that has an aromatic character, while the term "non-aromatic", as used herein, refers to a cyclic moiety, that may be saturated or unsaturated, e.g. polyunsaturated, but that does not have an aromatic character.

The term "phenyl" refers to a moiety of formula C₆H₅—, i.e.;

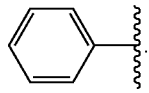

The term "benzyl" refers to a moiety of formula C₆H₅CH₂—, i.e.;

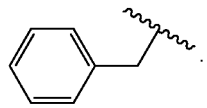 [SMILES: *Cc1ccccc1]

A "methylenedioxy biradical" is a biradical of formula —OCH₂O—.

An "ethylenedioxy biradical" is a biradical of formula —OCH₂CH₂O—.

"Treatment" as used herein includes prophylaxis of the named disorder or condition, or amelioration or elimination (i.e. cure) of the disorder once it has been established.

An "effective amount" refers to an amount of a compound that confers a therapeutic effect on the treated subject. The therapeutic effect may be objective (i.e., measurable by some test or marker, e.g. no measurable virus titre in a biological sample from the treated subject) or subjective (i.e., subject gives an indication of or feels an effect).

A "non-enveloped single-stranded (+) RNA viral infection" refers to an infection with a non-enveloped single-stranded (+) RNA virus.

A "non-enveloped virus" is a virus lacking viral envelope.

A "single-stranded (+) RNA virus" is a virus having genetic material which is single-stranded RNA and which RNA can be immediately translated to viral protein by the cell infected by the virus.

The term "mammal" refers to a human or any mammalian animal, e.g. a primate, a farm animal, a pet animal, or a laboratory animal. Examples of such animals are monkeys, cows, sheep, goats, horses, pigs, dogs, cats, rabbits, mice, rats etc. Preferably, the mammal is a human. In some embodiments, however, the mammal is an animal, e.g. a farm animal, such as a cow, sheep, goat, horse, or pigs. In some other embodiments, the animal is a pet, e.g. a dog, a cat or a rabbit.

The term "excipient" refers to pharmaceutically acceptable chemicals, such as known to those of ordinary skill in the art of pharmacy to aid the administration of the medicinal agent. It a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

Herein below, any reference to a compound of formula (I) or a compound of the invention, should be construed as referring to a compound for use according to the invention, as defined in the claims.

In a compound of formula (I)

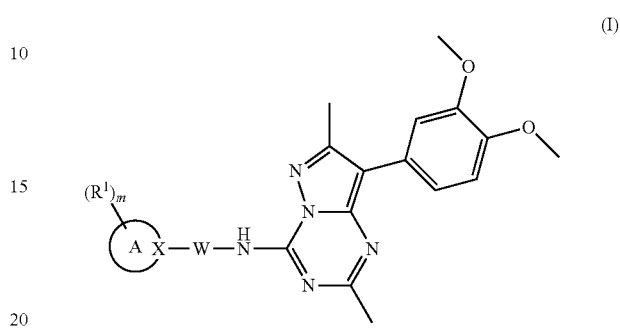

(I)

as defined herein above, W is CH₂ or CH₂CH₂. In some embodiments, W is CH₂. In some other embodiments, W is CH₂CH₂.

In ring A, the moiety X is C or CH. X is CH when attached to the two adjacent atoms in the ring by only single bonds, such as in cyclohexyl or tetrahydrofuryl, and X is C when X is attached by a double bond to an adjacent atom in the ring, such as in phenyl or cyclohexen-1-yl.

The ring A is 5- or 6-membered carbocyclyl or 5- or 6-membered heterocyclyl. In some embodiments, ring A is 5- or 6-membered carbocyclyl or 5- or 6-membered heteroaryl. In some embodiments, ring A is 5- or 6-membered carbocyclyl. In some embodiments, when A is 5- or 6-membered carbocyclyl, it more particularly is 6-membered carbocyclyl, e.g hexyl or phenyl, in particular phenyl.

In some embodiments, e.g. when ring A is phenyl, ring A is substituted by 1-3 moieties $R^1$, e.g. 1 or 2 moieties $R^1$, or 1 moiety $R^1$ (i.e. m is 1-3, m is 1 or 2, or m is 1). In some other embodiments, e.g. when ring A is phenyl, m is 0, 1 or 2, e.g. m is 0 or 1.

In some embodiments, when ring A is phenyl and m is an integer of from 1 to 3, e.g. m is 1 or 2, at least one $R^1$ is in meta position. In some embodiments, when ring A is phenyl, m is 1, and $R^1$ is in meta position.

In some particular embodiments, when ring A is phenyl and m is an integer of from 1 to 3, e.g. m is 1 or 2, and least one $R^1$ is in meta position, said $R^1$ in meta position is $R^9S(O)_2$, wherein $R^9$ is as defined herein, e.g. $R^9$ is C1-C3 alkyl, or $R^9$ is methyl. In some of these embodiments, m is 1. Furthermore, in some of these embodiments, W is CH₂; e.g. m is 1 and W is CH₂.

Thus, in some particular embodiments of a compound of formula (I), ring A is phenyl substituted in meta position, e.g. with a moiety $R^9S(O)_2$; m is 1, 2 or 3; e.g. m is 1 or 2; or m is 1; and W is CH₂.

In some embodiments, when ring A is phenyl and m is an integer of from 1 to 3, at least one $R^1$ is in para position.

In some embodiments, the compound of formula (I) may be represented by formula (Ia)

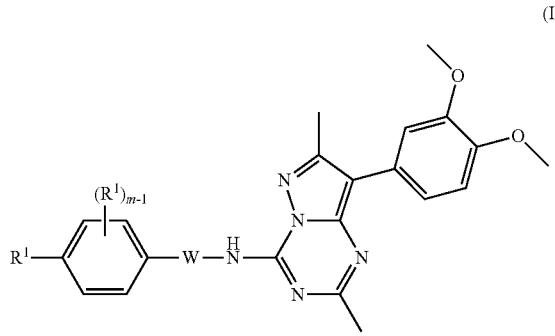
(Ia)

wherein m is 1, 2 or 3, and W and each $R^1$ are as defined herein.

When m is 1, the compound of formula (Ia) may be represented by formula (Ib)

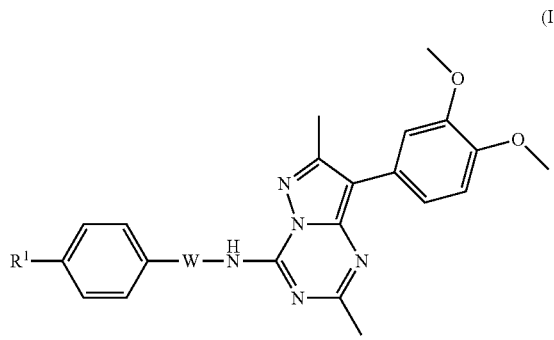
(Ib)

wherein W and $R^1$ are as defined herein.

In some embodiments of a compound of formula (Ib), W is $CH_2$ and the compound may be represented by formula (Ic)

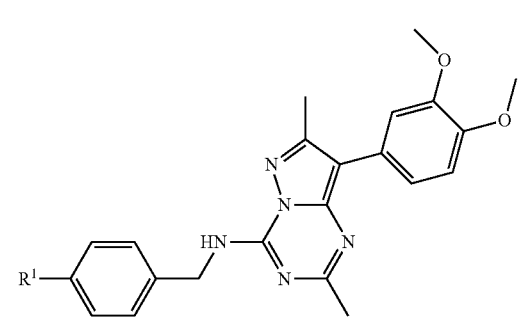
(Ic)

wherein $R^1$ is as defined herein.

In some other embodiments of a compound of formula (I), ring A is 5- or 6-membered heterocyclyl. When ring A is heterocyclyl, said heterocyclyl may contain 1, 2, 3 or 4 heteroatoms, e.g. 1, 2 or 3 heteroatoms, or 1 or 2 heteroatoms, e.g. 1 heteroatom, each heteroatom being independently selected from N, O and S, e.g. from O and S.

In some embodiments, when ring A is 5- or 6-membered heterocyclyl, it more particularly is 5-membered heterocyclyl. In some other embodiments, when ring A is 5- or 6-membered heterocyclyl, it more particularly is 6-membered heterocyclyl. In some embodiments, when ring A is 5- or 6-membered heterocyclyl, said heterocyclyl is aromatic, i.e. ring A is 5- or 6-membered heteroaryl. In some embodiments, ring A is 5-membered heteroaryl. In some other embodiments, ring A is 6-membered heteroaryl.

In some embodiments, ring A is 5-membered heteroaryl containing one or more heteroatoms, e.g. 1-3 heteroatoms; or 1 or 2 heteroatoms, of which at least one is N; e.g. ring A is pyrazolyl, oxazolyl, thiazolyl, thienyl or furyl.

In some embodiments, ring A is 5-membered heteroaryl containing 2 heteroatoms, of which at least one is N, e.g. ring A is pyrazolyl.

In some embodiments, ring A is 5-membered heteroaryl containing one heteroatom selected from O and S, i.e. ring A is thienyl or furyl, e.g. 2-thienyl or 2-furyl.

In some embodiments, ring A is 5-membered heteroaryl, and m is an integer of from 0 to 3, or from 0 to 2, e.g. m is 0 or 1. For example, in some embodiments, ring A is pyrazolyl, e.g. 1H-pyrazol-3-yl; m is 1, 2 or 3, e.g. m is 1 or 2, or m is 1, and at least one $R^1$ is attached to a ring nitrogen. For example, in some embodiments, ring A, substituted by one $R^1$, is selected from 1-$C_1$-$C_6$ alkyl-1H-pyrazol-3-yl, or 1-C1-C3 alkyl-1H-pyrazol-3-yl, in particular 1-methyl-1H-pyrazolyl-3yl, and is optionally substituted by one or two further $R^1$, e.g. one further $R^1$, or is substituted by no further $R^1$, i.e. m is 1. In some of these embodiments, W is $CH_2$.

In some embodiments, ring A is 6-membered heteroaryl. When ring A is 6-membered heteroaryl, said heteroaryl e.g. may be selected from pyridinyl, pyrimidinyl, or pyridazinyl, e.g. from pyridyl (also termed pyridinyl), i.e. pyridin-2-yl, pyridin-3-yl, pyridin-4-yl, in particular it may be pyridin-4-yl.

In some embodiments, e.g. of a compound of formula (If) as defined herein below, ring A is pyridin-3-yl or pyridin-4-yl. In some embodiments, ring A is pyridin-3-yl, e.g. ring A is pyridin-3-yl and m is 0, 1 or 2, e.g. m is 0 or 1. In some embodiments, ring A is pyridin-3-yl, m is 1, and $R^1$ is in para position; e.g. ring A is pyridin-3-yl, m is 1, and $R^1$ is in para position and is $R^2O$.

In some other embodiments, ring A is selected from 5- or 6-membered carbocyclyl, in particular 6-membered, carbocyclyl, such as phenyl and hexyl, and from 5- or 6-membered heterocyclyl containing one heteroatom only, e.g. tetrahydrofuryl, thienyl, furyl, and pyridyl.

In some other embodiments, ring A is phenyl or 5- or 6-membered heteroaryl. In some other embodiments, ring A is phenyl or 5-membered heteroaryl. In still other embodiments, ring A is phenyl or 6-membered heteroaryl.

In some embodiments, ring A is phenyl, said phenyl having a substituent $R^1$ in para position, and optionally being substituted by 1 or 2 further moieties $R^1$; or ring A is 6-membered heteroaryl having a heteroatom, e.g. nitrogen (N), in para position, said heteroaryl optionally being substituted by 1, 2 or 3 moieties $R^1$ and said heteroaryl optionally containing one or more further heteroatoms (e.g. N), e.g. 1 or 2 further N; or ring A is 6-membered heteroaryl having $N^+(O^-)$ in para position, said heteroaryl optionally being substituted by 1, 2 or 3 moieties $R^1$ and said heteroaryl optionally containing one or more further heteroatoms, e.g. 1 or 2 further N.

In some embodiments, ring A is phenyl having a substituent $R^1$ in para position, said phenyl optionally being substituted by 1 or 2 further moieties $R^1$; or ring A is 6-membered heteroaryl having a heteroatom, e.g. nitrogen (N), in para position, said heteroaryl optionally being substituted by 1, 2 or 3 moieties $R^1$ and said heteroaryl optionally containing one or more further heteroatoms (e.g. N), e.g. 1 or 2 further N.

In some embodiments, the compound of formula (I) may be one represented by formula (Id)

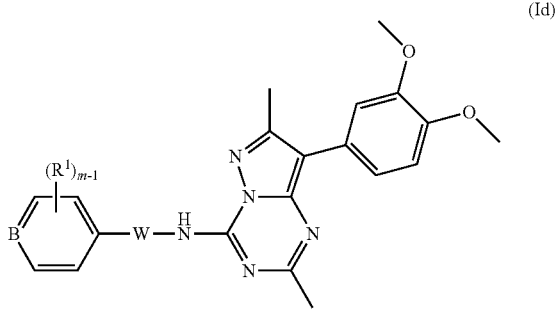

(Id)

wherein m is 1, 2, or 3, e.g. m is 1 or 2, in particular m is 1; B is N, $N^+(O^-)$ or $CR^1$, and W and each $R^1$ are as defined herein; e.g. W is $CH_2$.

In some embodiments of a compound of formula (Id), B is N or $N^+(O^-)$, in particular B is N.

In some embodiments, B is N, i.e. the compound may be represented by formula (Ie)

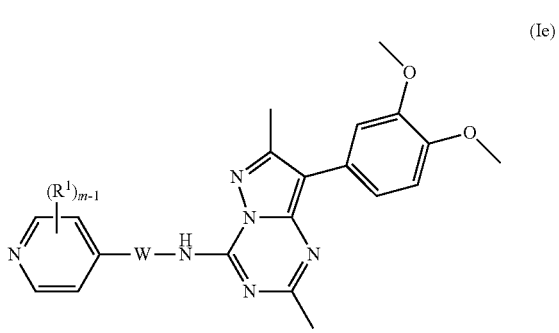

(Ie)

wherein m is 1, 2, or 3, e.g. m is 1 or 2, in particular m is 1; and W and each $R^1$ are as defined herein; e.g. W is $CH_2$.

In a compound of formula (I), m denotes the number of moieties $R^1$ attached to ring A, and is an integer of from 0 to 3. In some embodiments, m is an integer of from 1 to 3, e.g. m is 1 or 2. In some other embodiments, m is an integer of from 0 to 2, e.g. m is 0 or 1. In some embodiments, m is 1.

In a compound of formula (I), each $R^1$ is independently selected from C1-C6 alkyl optionally substituted by one or more halogen, $R^2O$, halogen, $R^3R^4NC(O)$, $R^5C(O)N(R^6)$, $R^7OC(O)$, $R^8C(O)O$, $R^9S(O)_2$, $R^{10}S(O)_2N(H)$, $R^{11}C(O)$, $R^{12}R^{13}N$, $^-O$ and $R^{14}R^{15}NS(O)_2$; and when m is at least 2, two $R^1$ attached to adjacent atoms of ring A may form, together with the atoms to which they are attached, a 5- or 6-membered heterocyclic or carbocyclic ring.

In some embodiments, each $R^1$ is independently selected from C1-C6 alkyl optionally substituted by one or more halogen, $R^2O$, halogen, $R^3R^4NC(O)$, $R^5C(O)N(R^6)$, $R^7OC(O)$, $R^8C(O)O$, $R^9S(O)_2$, $R^{10}S(O)_2N(H)$, $R^{11}C(O)$, $R^{12}R^{13}N$, and $R^{14}R^{15}NS(O)_2$; and when m is at least 2, two $R^1$ attached to adjacent atoms of ring A may form, together with the atoms to which they are attached, a 5- or 6-membered heterocyclic or carbocyclic ring.

In some embodiments, each $R^1$ is independently selected from C1-C6 alkyl, $R^2O$, halogen, $R^5C(O)N(R^6)$, $R^9S(O)_2$, $R^{10}S(O)_2N(H)$, $^-O$, and $R^{14}R^{15}NS(O)_2$.

When $R^1$ is C1-C6 alkyl, said alkyl e.g. may be selected from C1-C4 alkyl, e.g. C1-C3 alkyl, such as methyl, ethyl and isopropyl.

In the moieties $R^2O$, $R^3R^4NC(O)$, $R^5C(O)N(R^6)$, $R^7OC(O)$, $R^8C(O)O$, $R^9S(O)_2$, $R^{10}S(O)_2N(H)$, $R^{11}C(O)$, $R^{12}R^{13}N$, and $R^{14}R^{15}NS(O)_2$; each one $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from H and C1-C6 alkyl. In some embodiments, each one of $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from H and C1-C4 alkyl, e.g. from H and C1-C3 alkyl, or from H, methyl and ethyl, in particular from H and methyl.

In some other embodiments, each one of $R^2$, $R^3$, $R^4$, $R^5$, $R^6$, $R^7$, $R^8$, $R^9$, $R^{10}$, $R^{11}$, $R^{12}$, $R^{13}$ and $R^{14}$ is independently selected from C1-C6 alkyl, e.g. from C1-C4 alkyl, from C1-C3 alkyl, or from methyl and ethyl, in particular from methyl.

In some embodiments, in the moiety $R^5C(O)N(R^6)$, $R^5$ is as defined herein above, and $R^6$ is H.

In the moiety $R^{14}R^{15}NS(O)_2$, $R^{14}$ is as defined herein above, e.g. $R^{14}$ is H or $CH_3$, or $R^{14}$ is H, and $R^{15}$ is selected from H, C1-C6 alkyl, $R^{16}C(O)$, $R^{17}OC(O)$, and $R^{18}R^{19}NC(O)$. In some embodiments, $R^{15}$ is selected from H and C1-C6 alkyl, e.g. from H and C1-C4 alkyl, or from H and C1-C3 alkyl, such as H and $CH_3$. In some other embodiments, $R^{15}$ is selected from C1-C6 alkyl, $R^{16}C(O)$, $R^{17}OC(O)$, and $R^{18}R^{19}NC(O)$, e.g. from $R^{16}C(O)$, $R^{17}OC(O)$, and $R^{18}R^{19}NC(O)$.

In any of $R^{16}C(O)$, $R^{17}OC(O)$, and $R^{18}R^{19}NC(O)$, each one of $R^{16}$, $R^{17}$, $R^{18}$, and $R^{19}$ is independently selected from H and C1-C6 alkyl, e.g. from H and C1-C4 alkyl, or from H and C1-C3 alkyl, such as H and $CH_3$. In some embodiments, each one of $R^{16}$, $R^{17}$, $R^{18}$, and $R^{19}$ is independently selected from C1-C6 alkyl, e.g. from C1-C4 alkyl, or from C1-C3 alkyl, e.g. each is $CH_3$.

When $R^1$ is halogen, said halogen e.g. may be selected from F, Cl and Br. In some embodiments, when $R^1$ is halogen, said halogen is F or Cl, in particular Cl. In some other embodiments, when $R^1$ is halogen, said halogen is F.

When $R^1$ is an alkyl moiety or comprises an alkyl moiety, any such alkyl moiety may be substituted by one or more halogen, in particular one or more F.

When any $R^1$ is $^-O$, said $^-O$ preferably is attached to a nitrogen atom in ring A, i.e. ring A is nitrogen-containing heterocyclyl.

In some embodiments, when m is at least 2, e.g. m is 2, two $R^1$ attached to adjacent atoms of the ring A form, together with the atoms to which they are attached, a 5- or 6-membered heterocyclic or carbocyclic ring, e.g. a 5- or 6-membered heterocyclic ring, such as a 5- or 6-membered ring containing one or two oxygen atoms. For example, two $R^1$ attached to adjacent atoms of ring A may form together a methylenedioxy biradical or an ethylenedioxy biradical.

In some embodiments, when two $R^1$ attached to adjacent atoms of the ring A form, together with the atoms to which they are attached, a 5- or 6-membered heterocyclic or carbocyclic ring, said ring is a 5-membered heterocyclic ring, e.g. 1,3-dioxole or 1,3-dioxolane.

It should be realized that features of the various embodiments described herein may be freely combined within the scope of the present invention, unless mutually incompatible, or unless otherwise specified.

For example, in some embodiments, wherein W is CH$_2$, the compound is as represented by formula (If)

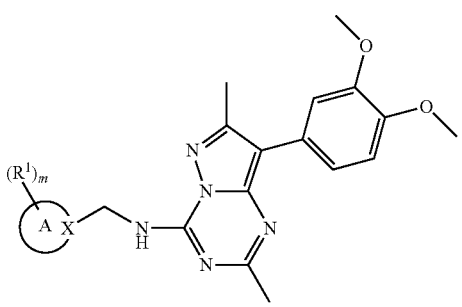

(If)

wherein
X is C;
ring A is phenyl or 5- or 6-membered heteroaryl;
m is an integer of from 0 to 3; e.g. from 0 to 2; or m is 0 or 1:
and each R$^1$ is as defined herein above.

In some embodiments of a compound of formula (If), each R$^1$ is independently selected from C1-C6 alkyl optionally substituted by one or more halogen, R$^2$O, halogen, R$^5$C(O)N(R$^6$), R$^9$S(O)$_2$, R$^{10}$S(O)$_2$N(H), and R$^{14}$R$^{15}$NS(O)$_2$; and when m is at least 2, two R$^1$ attached to adjacent atoms of ring A may form, together with the atoms to which they are attached, a 5- or 6-membered heterocyclic or carbocyclic ring, e.g. a 5- or 6-membered saturated or mono-unsaturated heterocyclic or carbocyclic ring, in particular a ring formed by methylenedioxy biradical or an ethylenedioxy biradical attached to adjacent atoms of ring A;
each R$^2$, R$^5$, R$^6$, R$^9$, R$^{10}$, and R$^{14}$ is independently selected from H and C1-C6 alkyl, wherein any alkyl is optionally substituted by one or more halogen;
R$^{15}$ is selected from H, C1-C6 alkyl, R$^{16}$C(O), R$^{17}$OC(O), and R$^{18}$R$^{19}$NC(O); and
each R$^{16}$, R$^{17}$, R$^{18}$, and R$^{19}$ is independently selected from H and C1-C6 alkyl, wherein any alkyl is optionally substituted by one or more halogen.

In some of these embodiments, each R$^1$ is independently selected from C1-C6 alkyl optionally substituted by one or more halogen, R$^2$O, halogen, R$^5$C(O)N(R$^6$), R$^9$S(O)$_2$, R$^{10}$S(O)$_2$N(H), and R$^{14}$R$^{15}$NS(O)$_2$; and when m is at least 2, two R$^1$ attached to adjacent atoms of ring A may form, together with the atoms to which they are attached, a 5- or 6-membered heterocyclic or carbocyclic ring, e.g. a 5- or 6-membered saturated or mono-unsaturated heterocyclic or carbocyclic ring, in particular a ring formed by methylenedioxy biradical or an ethylenedioxy biradical attached to adjacent atoms of ring A;
each R$^2$, R$^5$, R$^6$, R$^9$, R$^{10}$, and R$^{14}$ is independently selected from H and C1-C6 alkyl, wherein any alkyl is optionally substituted by one or more halogen; and
R$^{15}$ is selected from H and C1-C6 alkyl, and wherein any alkyl is optionally substituted by one or more halogen.

In the above embodiments, any C1-C6 alkyl preferably is C1-C3 alkyl, e.g. C1-C2 alkyl, in particular CH$_3$.

Moreover, when any alkyl is substituted by one or more halogen, each such halogen preferably is F. For example, in some embodiments of a compound of formula (If), each R$^1$ is selected from F, Cl, CF$_3$, CH$_3$, CH$_3$C(O)NH, CH$_3$O, CH$_3$S(O)$_2$, NH$_2$S(O)$_2$, OH, CH$_3$S(O)$_2$NH, and CH$_3$NHS(O)$_2$, or two R$^1$, attached to adjacent atoms of ring A, form together a methylenedioxy biradical.

In some of these embodiments, when ring A is phenyl, m is an integer of from 1 to 3, e.g. from 1 to 2, in particular m is 1; and when ring A is heteroaryl, m is an integer of from 0 to 2, e.g. m is 0 or 1.

In some embodiments of a compound of formula (If), ring A is phenyl and m is 1 or 2, or A is 5- or 6-membered heteroaryl and m is 0 or 1.

In some embodiments, ring A is phenyl or 5- or 6-membered heteroaryl and m is 0 or 1. In some of these embodiments, ring A is phenyl. In some other of these embodiments, ring A is 5- or 6-membered heteroaryl. In some of these embodiments, ring A is 6-membered heteroaryl. In some other of these embodiments, ring A is 5-membered heteroaryl.

In some embodiments of a compound of formula (I), e.g. a compound of formula (If), ring A is selected from phenyl, pyridyl, thienyl, furyl, pyrazolyl, oxazolyl, pyridmidinyl, and pyridazinyl.

In some embodiments of a compound of formula (I), e.g. a compound of formula (If), ring A is phenyl. In some other of these embodiments, when ring A is 5-membered heteroaryl, it more particularly is selected from thienyl, furyl, pyrazolyl, and oxazolyl.

In some embodiments of a compound of formula (I), e.g. a compound of formula (If), when ring A is 6-membered heteroaryl, it more particularly is selected from 6-membered heteroaryl containing one or more nitrogen atoms in the ring, e.g. 1 or 2 N, e.g. ring A is selected from pyridinyl, pyridmidinyl, and pyridazinyl.

The compounds of the invention may be readily synthesized by the person of ordinary skill e.g. by following the general procedure outlined in Reaction Scheme 1.

Reaction Scheme 1

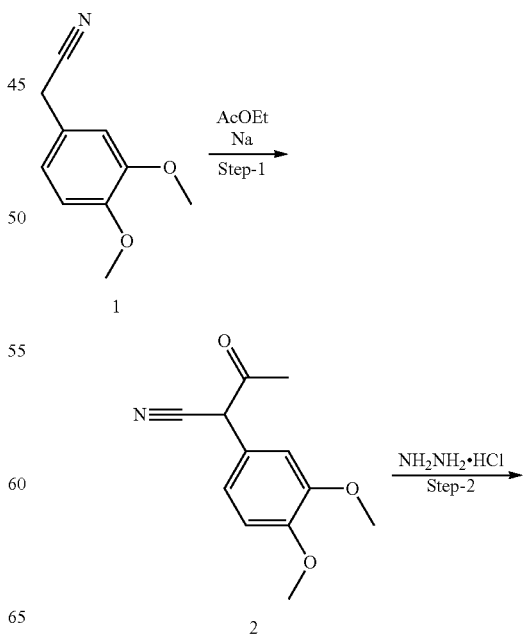

-continued

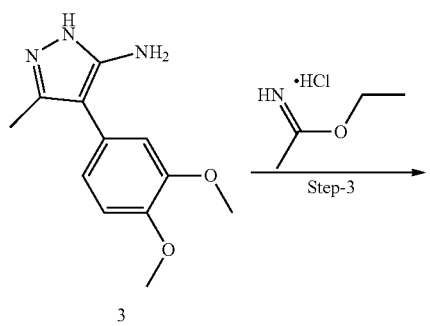

3

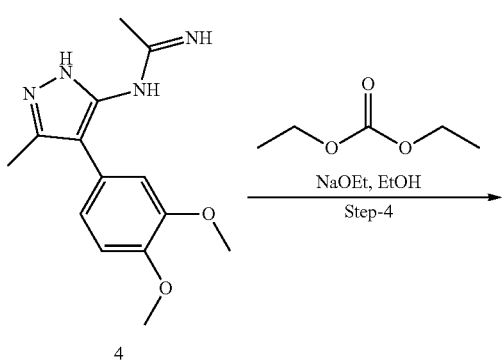

4

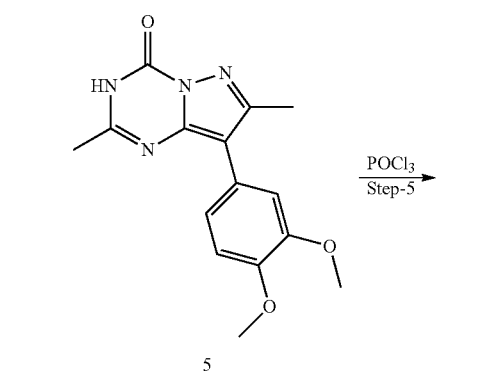

5

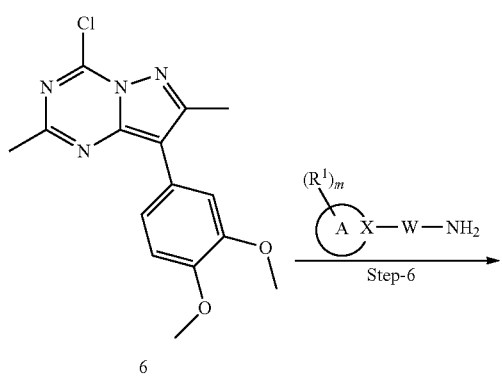

6

-continued

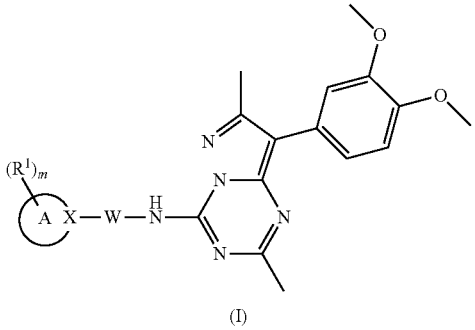

(I)

The compounds may also be synthesized using methods similar to those described in Mejdrova et al (J. Med. Chem., 2015, 58 (9), pp 3767-3793) or Long et al (J. Org. Chem., 2015, 80, 4716-4721).

The compounds of formula (I) also may be transformed into suitable, pharmaceutically acceptable salts. The term pharmaceutically acceptable salt of a compound refers to a salt that is pharmaceutically acceptable, as defined herein, and that possesses the desired pharmacological activity of the parent compound. Pharmaceutically acceptable salts include acid addition salts formed with inorganic acids, e.g. hydrochloric acid, hydrobromic acid, sulphuric acid, nitric acid, phosphoric acid; or formed with organic acids, e.g. acetic acid, benzenesulfonic acid, benzoic acid, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, etc.

In the preparation of acid addition salts, preferably such acid are used which form suitably therapeutically acceptable salts. Examples of such acids are hydrohalogen acids, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Whenever a chiral carbon is present in a chemical structure, it is intended that all stereoisomers associated with that chiral carbon are encompassed by the structure, unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic mixture, or one stereoisomer only.

The present invention includes pharmaceutical compositions comprising at least one compound of formula (I), or an individual isomer, racemic or non-racemic mixture of isomers or a pharmaceutically acceptable salt thereof, together with at least one pharmaceutically acceptable excipient, e.g. a carrier, and optionally other therapeutic and/or prophylactic ingredients.

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilising agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and cholorobutanol.

For inhalation or nasal administration, suitable pharmaceutical formulations are as particles, aerosols, powders, mists or droplets, e.g. with an average size of about 10 µm in diameter or less. For example, compositions for inhalation may be prepared as solutions in saline, employing benzyl alcohol or other suitable preservatives, absorption promoters to enhance bioavailability, fluorocarbons, and/or other solubilising or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery.

The composition may be formulated as a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water.

Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water.

The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient.

In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compound of the present invention is contemplated as useful for the treatment of diseases caused by RNA viral infection in a mammal, e.g. non-enveloped single-stranded (+) RNA viral infection, in particular diseases caused by picornaviruses, which is either a human or animal, but preferably a human. The picornavirus e.g. may be a Parechovirus (e.g. Ljungan or Parecho), a Cardiovirus (e.g. EMCV or Theiler's virus), Enterovirus (e.g. EV, Coxsackie, Polio, Rhino) or a hepatovirus. For veterinary use, the picornavirus may be e.g. an Aphthovirus or a Teschovirus.

In some embodiments, the viral disease is one linked to or caused by an enterovirus, a coxsackie virus; or a polio virus.

In some embodiments, the viral disease is one linked to or caused by an enterovirus. In some embodiments, the viral disease is one linked to or caused by a coxsackie virus. In some embodiments, the viral disease is one linked to or caused by a polio virus.

Diseases that are considered to be linked to, caused by, or otherwise associated with virus infection, e.g. by picornaviruses, are e.g. neurodegenerative diseases such as multiple sclerosis, Parkinson's disease, amyotrophic lateral sclerosis, Alzheimer's disease, Huntington's disease, poliomyelitis, encephalitis, meningitis, sepsis, cancer, paralysis, myocarditis, diabetes, common cold, hand-foot-and-mouth disease, herpangina, pleurodynia, diarrhea, mucocutaneous lesions, respiratory illness, conjunctivitis, myositis, and chronic fatigue syndrome.

The present invention consequently also includes a compound of formula (I) for use in the treatment of any of the above mentioned conditions, as well as the use of a compound of formula (I) in the manufacturing of a medicament for the treatment of any of the above mentioned conditions and a method of treatment of any of the above mentioned conditions, by administering to an animal or human in need thereof, a compound of formula (I).

The invention is further illustrated by some non-limiting examples.

EXAMPLES

A number of compounds of the inventions (Examples 1-32) were synthesized by following the general procedure illustrated in Reaction Scheme 1, as described herein below:

Step-1

To a solution of 1 (10.0 g, 56.4 mmol) in ethyl acetate (200 mL) was added sodium metal (2.6 g, 112.8 mmol) portion wise at 0-5° C. under nitrogen atmosphere. The reaction mixture was stirred at room temperature for 6 h. The progress of the reaction was monitored by TLC. After completion, the reaction mixture was cooled to 0-5° C., quenched with methanol (50 mL) and the solvent was evaporated under pressure. The resultant solid was dissolved in water (100 mL) and washed with toluene (2×100 mL). The aqueous solution was acidified with acetic acid (pH 4 to 5) and extracted with dichloromethane (3×100 mL). The combined organic layer was washed with water, brine, dried over sodium sulphate, filtered and concentrated under reduced pressure. The crude material was purified by recrystallization using ethyl acetate and hexane to afford 2 (9.5 g, 76.8%) as pale brown solid.

Step-2

To a solution of 2 (9.0 g, 41.05 mmol) in ethanol (90 mL) was added hydrazine monohydrochloride (4.218 g, 61.57 mmol) and acetic acid (2.7 mL, 2.83 g, 47.166 mmol) at room temperature under nitrogen atmosphere. The reaction mixture was heated to 85° C. and stirred for 5-6 h. The reaction was monitored by TLC. After completion of the reaction, the reaction mixture was cooled to room temperature. The reaction mixture was quenched with water (90 mL), concentrated under reduced pressure. The resultant aqueous layer was washed with toluene (3×45 mL) and basified with 10% aq. sodium bicarbonate solution (pH: 8-9). The aqueous layer was extracted with dichloromethane (4×50 mL). The combined organic layer was washed with water, brine, dried over sodium sulphate and concentrated under reduced pressure to afford 3 (7.6 g, 79.36%) as an off-white solid. The product obtained was used without further purification.

Step-3:

To a suspension of 3 (3.0 g, 12.86 mmol) in acetonitrile (75 mL) was added DIPEA until the reaction mixture showed pH in the range of 9-10. To the reaction mixture was added ethyl acetimidate hydrochloride (2.38 g, 19.26 mmol) at room temperature under nitrogen atmosphere. The reaction mixture was again basified with DIPEA (pH 9-10). To the mixture was added acetic acid (0.77 mL, 12.8 mmol) and the mixture was stirred for 16 h at room temperature. The reaction mixture then was diluted with diethyl ether (30 mL), the solid formed was filtered and dried under reduced pressure at 50-55° C. to get 4 (2.5 g, 70.86%) as a colorless solid.

Step-4:

Sodium metal (0.628 g, 27.3 mmol) was dissolved in absolute ethanol (18 mL) at room temperature under nitrogen atmosphere. To the clear solution were added 4 (0.6 g, 2.187 mmol) and diethyl carbonate (2.65 mL, 21.8 mmol) at room temperature and the reaction mixture was heated to reflux for 16 h. The progress of the reaction was monitored by TLC. After completion, the reaction mixture was cooled to room temperature and quenched with water (30 mL). The resultant mass was concentrated under reduced pressure at 50-55° C. The residue was diluted with water, acidified with acetic acid (pH 5-6), extracted with dichloromethane (3×10 mL), the combined organic extract was washed with water, brine, dried over sodium sulphate, filtered and concentrated under reduced pressure to afford 5 (0.420 g, 63.94%) as colorless solid.

Step-5:

To a suspension of 5 (0.7 g, 2.331 mmol) in dry toluene (15 mL) were added phosphoryl chloride (5.44 mL, 8.948 g, 58.36 mmol) and N,N-diethyl aniline (0.748 mL, 0.7 g, 4.702 mmol) at room temperature under nitrogen atmosphere. The reaction mixture was then heated to 105° C. for 16 h. After 16 h, the reaction mixture was concentrated under reduced pressure at 50-55° C. and co-evaporated with toluene under reduced pressure. The crude material 6 (0.53 g, quantitative) obtained was used as such without further purification.

Step-6:

To a solution of 6 (1.0 eq.) in toluene or acetonitrile or DMF (10-20 V) were added the respective amine (1.3 eq.) and base [DIPEA (5 V)/$K_2CO_3$/KO$^t$Bu/NaH (2.0 eq.)] sequentially. The reaction mixture was then stirred at room temperature or at 90° C. for 16 h. The progress of the reaction was monitored by TLC. The reaction mixture was cooled to room temperature and concentrated under reduced pressure. The residue was diluted with water (20 V), extracted with dichloromethane (3×10 V). The combined organic extract was washed with water, brine, dried over sodium sulphate, filtered and concentrated under reduced pressure. The crude material was purified by flash column chromatography (silica gel, 50% EtOAc in Hexane) to afford the desired compound of formula (I) with >95% HPLC purity.

The chemical names of the compounds of Examples 1-32 are given in Table 1.

TABLE 1

| Ex. | Chemical name |
|---|---|
| 1 | 8-(3,4-dimethoxyphenyl)-N-[(4-fluorophenyl)methyl]-2,7-dimethyl-pyrazolo[1,5-a][1,3,5]triazin-4-amine |
| 2 | 8-(3,4-dimethoxyphenyl)-2,7-dimethyl-N-[[4-(trifluoromethyl)phenyl]methyl]pyrazolo[1,5-a][1,3,5]triazin-4-amine |
| 3 | 8-(3,4-dimethoxyphenyl)-2,7-dimethyl-N-(p-tolylmethyl)pyrazolo[1,5-a][1,3,5]triazin-4-amine |
| 4 | 8-(3,4-dimethoxyphenyl)-N-[(4-isopropylphenyl)methyl]-2,7-dimethyl-pyrazolo[1,5-a][1,3,5]triazin-4-amine |
| 5 | 8-(3,4-dimethoxyphenyl)-2,7-dimethyl-N-(2-pyridylmethyl)pyrazolo[1,5-a][1,3,5]triazin-4-amine |
| 6 | 8-(3,4-dimethoxyphenyl)-2,7-dimethyl-N-(4-pyridylmethyl)pyrazolo[1,5-a][1,3,5]triazin-4-amine |
| 7 | N-[2-(4-chlorophenyl)ethyl]-8-(3,4-dimethoxyphenyl)-2,7-dimethyl-pyrazolo[1,5-a][1,3,5]triazin-4-amine |
| 8 | N-[(4-chlorophenyl)methyl]-8-(3,4-dimethoxyphenyl)-2,7-dimethyl-pyrazolo[1,5-a][1,3,5]triazin-4-amine |
| 9 | N-[4-[[[8-(3,4-dimethoxyphenyl)-2,7-dimethyl-pyrazolo[1,5-a][1,3,5]triazin-4-yl]amino]methyl]phenyl]acetamide |
| 10 | 8-(3,4-dimethoxyphenyl)-N-[(4-methoxyphenyl)methyl]-2,7-dimethyl-pyrazolo[1,5-a][1,3,5]triazin-4-amine |
| 11 | 8-(3,4-dimethoxyphenyl)-2,7-dimethyl-N-[(3-methylsulfonylphenyl)methyl]pyrazolo[1,5-a][1,3,5]triazin-4-amine |
| 12 | 8-(3,4-dimethoxyphenyl)-2,7-dimethyl-N-[(1-oxidopyridin-1-ium-4-yl)methyl]pyrazolo[1,5-a][1,3,5]triazin-4-amine |
| 13 | 8-(3,4-dimethoxyphenyl)-N-[(6-methoxy-3-pyridyl)methyl]-2,7-dimethyl-pyrazolo[1,5-a][1,3,5]triazin-4-amine |
| 14 | 4-[[[8-(3,4-dimethoxyphenyl)-2,7-dimethyl-pyrazolo[1,5-a][1,3,5]triazin-4-yl]amino]methyl]benzenesulfonamide |
| 15 | N-(cyclohexylmethyl)-8-(3,4-dimethoxyphenyl)-2,7-dimethyl-pyrazolo[1,5-a][1,3,5]triazin-4-amine |
| 16 | N-(1,3-benzodioxol-5-ylmethyl)-8-(3,4-dimethoxyphenyl)-2,7-dimethyl-pyrazolo[1,5-a][1,3,5]triazin-4-amine |
| 17 | 4-[[[8-(3,4-dimethoxyphenyl)-2,7-dimethyl-pyrazolo[1,5-a][1,3,5]triazin-4-yl]amino]methyl]phenol |
| 18 | 8-(3,4-dimethoxyphenyl)-2,7-dimethyl-N-(tetrahydrofuran-2-ylmethyl)pyrazolo[1,5-a][1,3,5]triazin-4-amine |
| 19 | N-[4-[[[8-(3,4-dimethoxyphenyl)-2,7-dimethyl-pyrazolo[1,5-a][1,3,5]triazin-4-yl]amino]methyl]phenyl]methanesulfonamide |
| 20 | N-benzyl-8-(3,4-dimethoxyphenyl)-2,7-dimethyl-pyrazolo[1,5-a][1,3,5]triazin-4-amine |
| 21 | 8-(3,4-dimethoxyphenyl)-2,7-dimethyl-N-(2-thienylmethyl)pyrazolo[1,5-a][1,3,5]triazin-4-amine |
| 22 | 8-(3,4-dimethoxyphenyl)-2,7-dimethyl-N-(3-pyridylmethyl)pyrazolo[1,5-a][1,3,5]triazin-4-amine |
| 23 | 8-(3,4-dimethoxyphenyl)-2,7-dimethyl-N-[(5-methyl-2-furyl)methyl]pyrazolo[1,5-a][1,3,5]triazin-4-amine |
| 24 | methyl N-[4-[[[8-(3,4-dimethoxyphenyl)-2,7-dimethyl-pyrazolo[1,5-a][1,3,5]triazin-4-yl]amino]methyl]phenyl]sulfonylcarbamate |
| 25 | N-[4-[[[8-(3,4-dimethoxyphenyl)-2,7-dimethyl-pyrazolo[1,5-a][1,3,5]triazin-4-yl]amino]methyl]phenyl]sulfonylpropanamide |
| 26 | N-methyl-4-[[[8-(3,4-dimethoxyphenyl)-2,7-dimethyl-pyrazolo[1,5-a][1,3,5]triazin-4-yl]amino]methyl]benzenesulfonamide |
| 27 | 8-(3,4-dimethoxyphenyl)-2,7-dimethyl-N-[(1-methyl-1H-pyrazol-3-yl)methyl]pyrazolo[1,5-a][1,3,5]triazin-4-amine |
| 28 | 8-(3,4-dimethoxyphenyl)-2,7-dimethyl-N-[(1,3-oxazol-5-yl)methyl]pyrazolo[1,5-a][1,3,5]triazin-4-amine |

TABLE 1-continued

| Ex. | Chemical name |
|---|---|
| 29 | 8-(3,4-dimethoxyphenyl)-2,7-dimethyl-N-[(piperidin-4-yl)methyl]pyrazolo[1,5-a][1,3,5]triazin-4-amine |
| 30 | 8-(3,4-dimethoxyphenyl)-2,7-dimethyl-N-[(2-methylpyrimidin-5-yl)methyl]pyrazolo[1,5-a][1,3,5]triazin-4-amine |
| 31 | 8-(3,4-dimethoxyphenyl)-2,7-dimethyl-N-[(pyridazin-4-yl)methyl]pyrazolo[1,5-a][1,3,5]triazin-4-amine |
| 32 | 8-(3,4-dimethoxyphenyl)-2,7-dimethyl-N-[(6-methylpyridin-3-yl)methyl]pyrazolo[1,5-a][1,3,5]triazin-4-amine |

The structural formulas of the compounds of Examples 1-32 are shown in Table 2.

TABLE 2

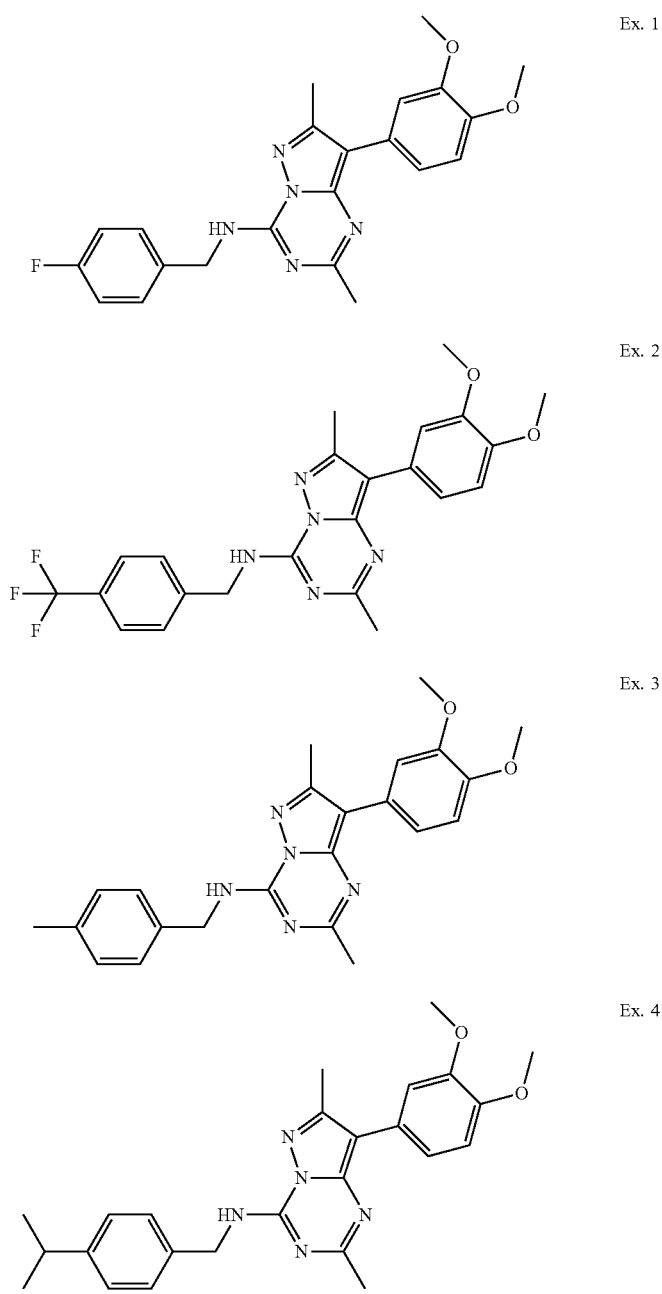

TABLE 2-continued
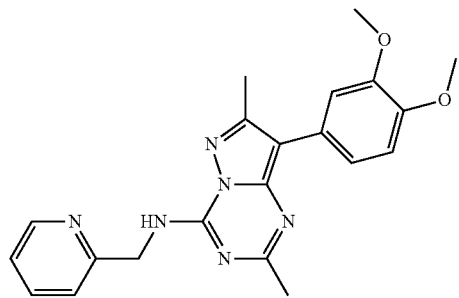 [SMILES: COc1ccc(-c2c(C)nn3c(NCc4ccccn4)nc(C)nc23)cc1OC]
Ex. 5
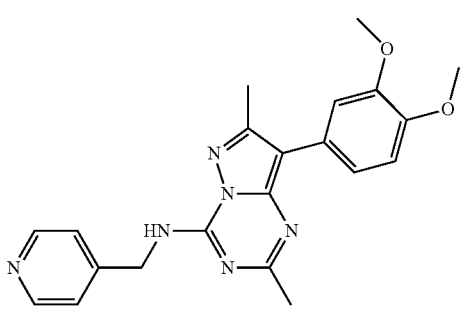 [SMILES: COc1ccc(-c2c(C)nn3c(NCc4ccncc4)nc(C)nc23)cc1OC]
Ex. 6
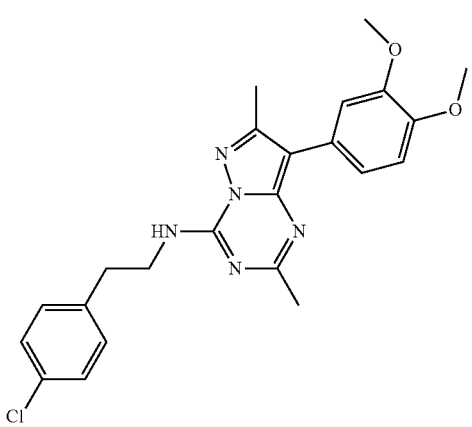 [SMILES: COc1ccc(-c2c(C)nn3c(NCCc4ccc(Cl)cc4)nc(C)nc23)cc1OC]
Ex. 7
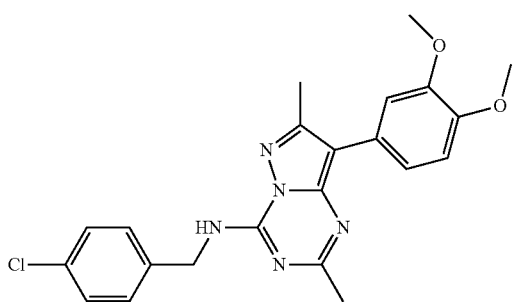 [SMILES: COc1ccc(-c2c(C)nn3c(NCc4ccc(Cl)cc4)nc(C)nc23)cc1OC]
Ex. 8

TABLE 2-continued
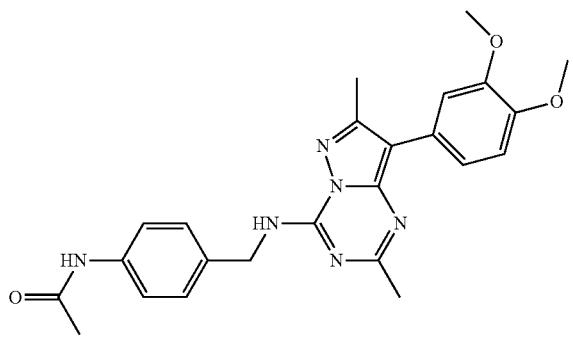 [SMILES: COc1ccc(-c2c(C)nn3c(NCc4ccc(NC(C)=O)cc4)nc(C)nc23)cc1OC]
Ex. 9
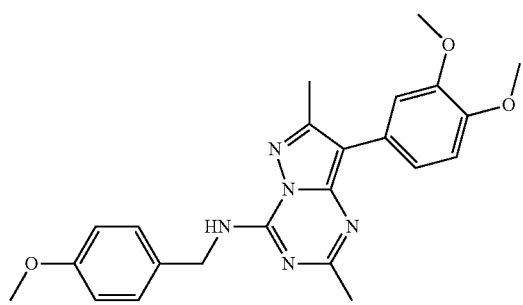
Ex. 10
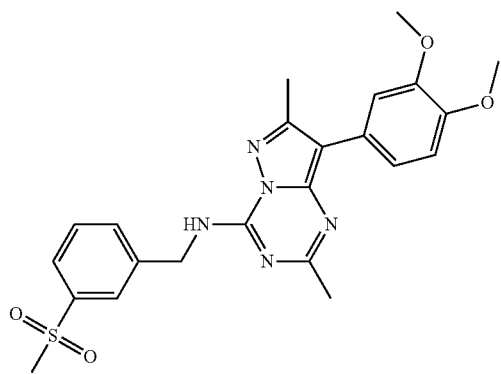 [SMILES: COc1ccc(-c2c(C)nn3c(NCc4cccc(S(C)(=O)=O)c4)nc(C)nc23)cc1OC]
Ex. 11
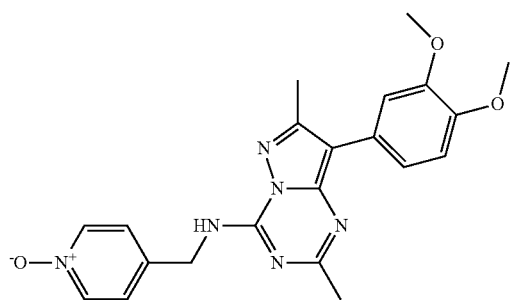
Ex. 12
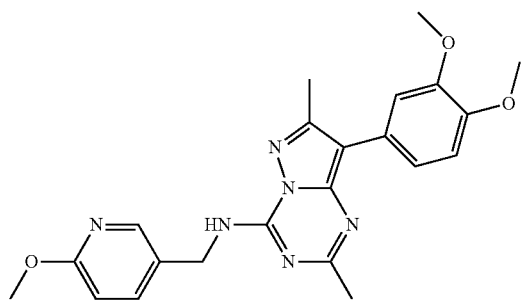
Ex. 13

TABLE 2-continued
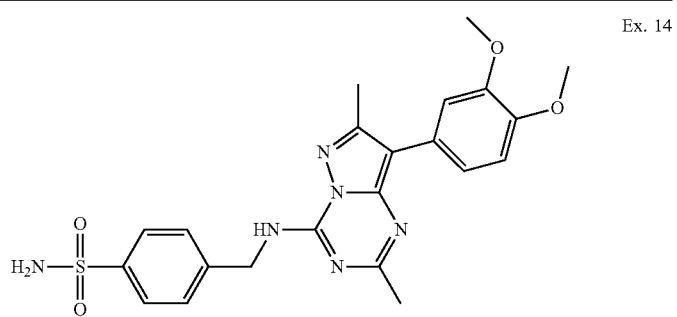
Ex. 14
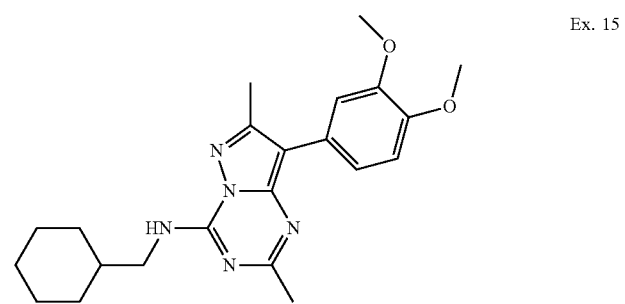
Ex. 15
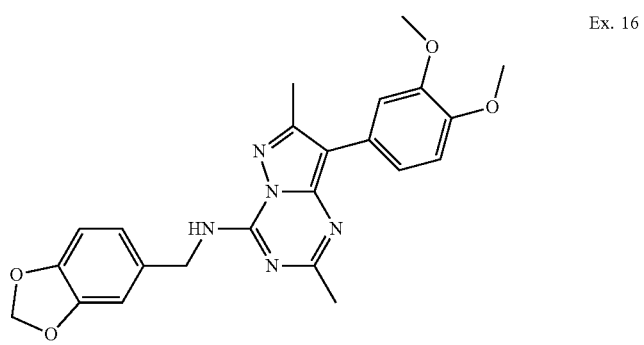
Ex. 16
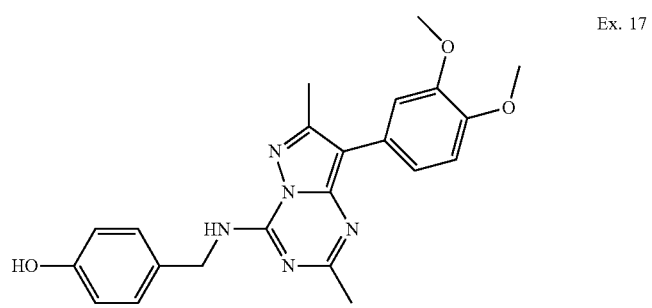
Ex. 17
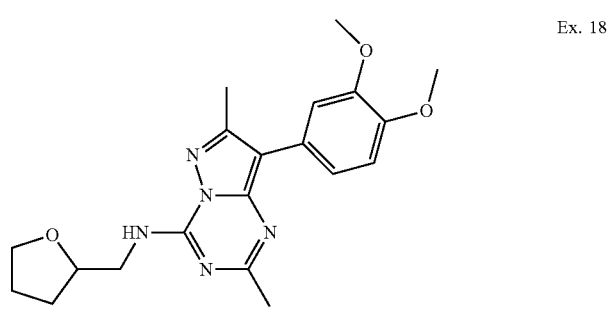
Ex. 18

TABLE 2-continued
Ex. 19
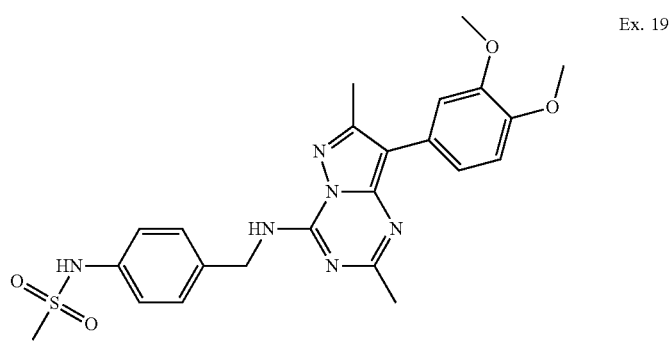
Ex. 20
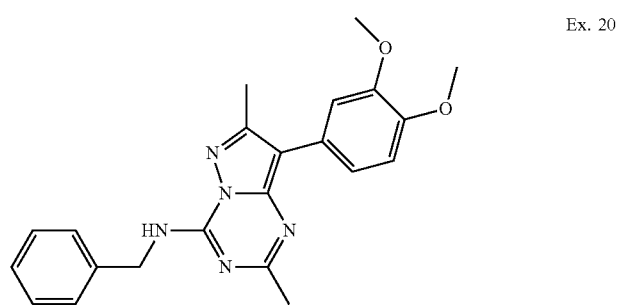
Ex. 21
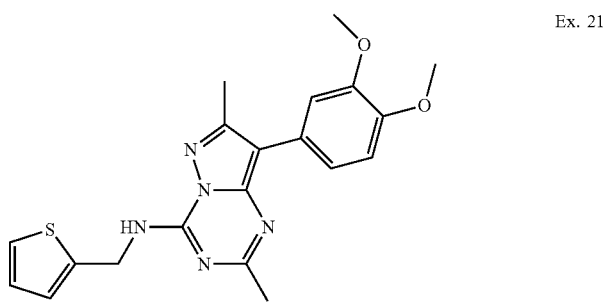
Ex. 22
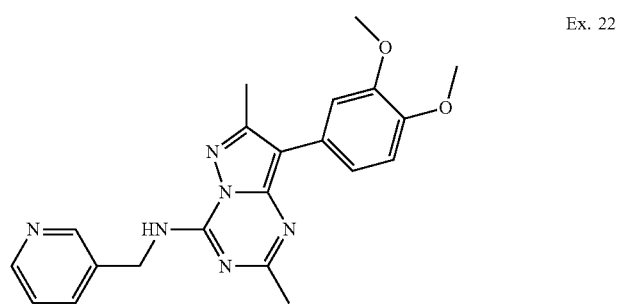
Ex. 23
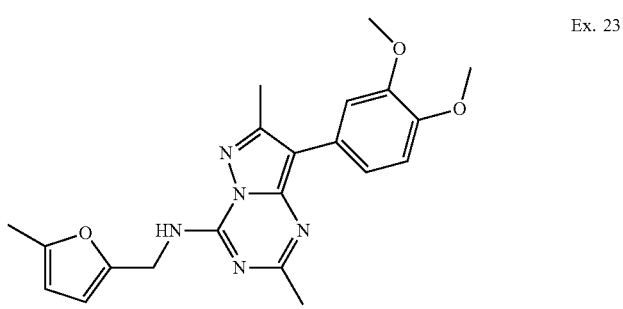

TABLE 2-continued
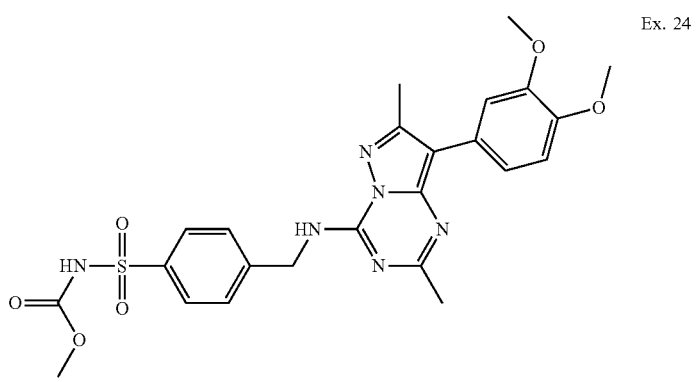
Ex. 24
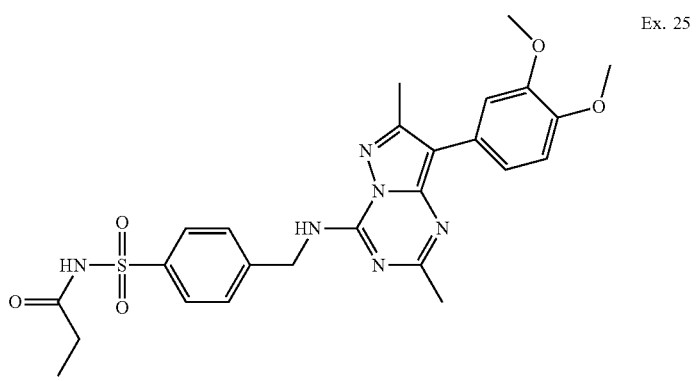
Ex. 25
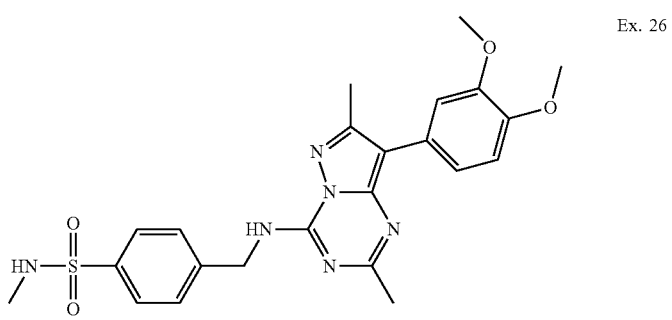
Ex. 26
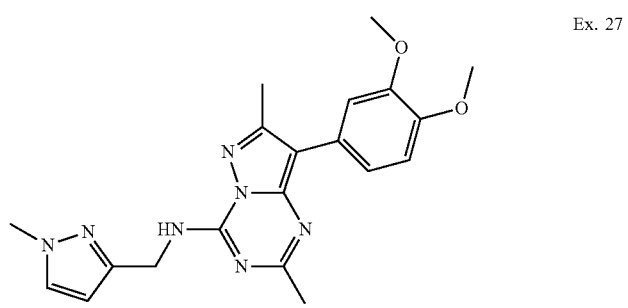
Ex. 27

TABLE 2-continued
| | |
|---|---|
| 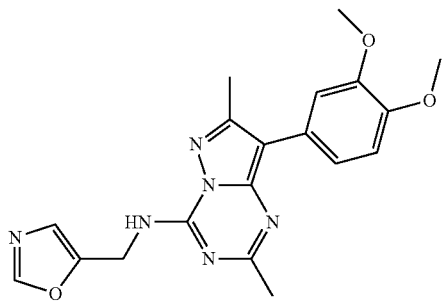 [SMILES: COc1ccc(-c2c(C)nn3c(NCc4cnco4)nc(C)nc23)cc1OC] | Ex. 28 |
| 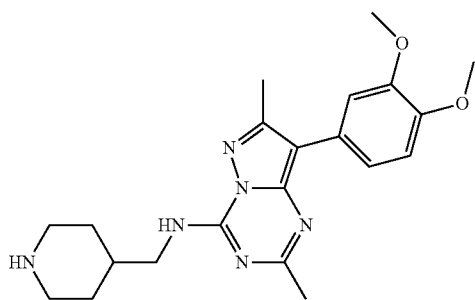 [SMILES: COc1ccc(-c2c(C)nn3c(NCC4CCNCC4)nc(C)nc23)cc1OC] | Ex. 29 |
| 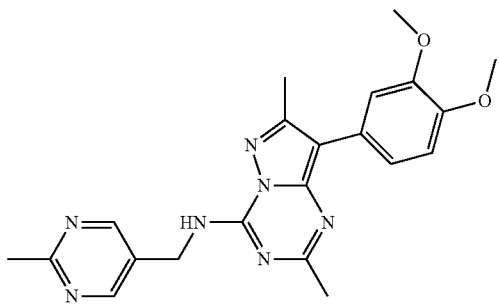 | Ex. 30 |
| 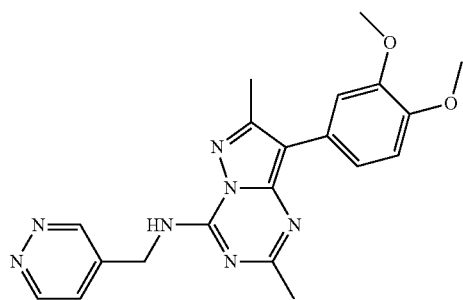 [SMILES: COc1ccc(-c2c(C)nn3c(NCc4ccnnc4)nc(C)nc23)cc1OC] | Ex. 31 |
| 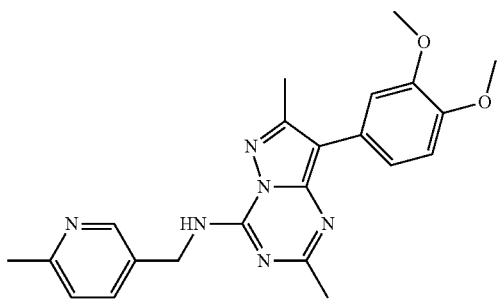 | Ex. 32 |

Analytical data for the compounds of Examples 1-32 are shown in Table 3.

TABLE 3

| Ex. | Analytical Data |
|---|---|
| 1 | $^1$H-NMR (DMSO, 300 MHz): δ 8.35 (t, 1 H), 7.42 (t, 2 H), 7.12 (t, 2 H), 7.03 (d, 1 H), 6.93 (d, 1 H), 6.66 (s, 1 H), 4.66 (d, 2 H), 3.78 (d, 6 H), 2.44 (s, 3 H), 2.24 (s, 3 H), LCMS: 407.6 [M + H], HPLC purity: 99.98% |
| 2 | $^1$H-NMR (MeOD, 300 MHz): δ 7.31 (d, 2 H), 7.23 (d, 1 H), 7.17 (d, 2 H), 7.10 (d, 1 H), 7.05 (d, 1 H), 4.79 (d, 2 H), 3.89 (d, 6 H), 2.50 (s, 3 H), 2.46 (s, 3 H), 2.33 (s, 3 H), LCMS: 404.6 [M + H], HPLC purity: 99.59% |
| 3 | $^1$H-NMR (CDCl3, 300 MHz): δ 7.65 (d, 2 H), 7.55 (d, 2 H), 7.18 (d, 1 H), 6.98 (d, 1 H), 6.81 (d, 1 H), 4.95 (d, 2 H), 3.96 (d, 6 H), 2.57 (s, 3 H), 2.55 (s, 3 H), LCMS: 458.6 [M + H], HPLC purity: 99.89% |
| 4 | $^1$H-NMR (MeOD, 300 MHz): δ 7.33 (d, 2 H), 7.22 (t, 3 H), 7.09 (d, 1 H), 7.04 (d, 1 4 H), 4.79 (s, 2 H), 3.89 (d, 6 H), 2.89 (m, 1 H), 2.49 (s, 3 H), 2.46 (s, 3 H), 1.25 (s, 3 H), 1.29 (s, 3 H), LCMS: 432.7 [M + H], HPLC purity: 99.87% |
| 5 | $^1$H-NMR (MeOD, 300 MHz): δ 8.55 (d, 1 H), 7.83 (t, 1 H), 7.50 (d, 1 H), 7.35 (dd, 1 H), 7.25 (d, 1 H), 7.12 (dd, 1 H), 7.05 (d, 1 H), 4.96 (s, 2 H), 3.89 (d, 6 H), 2.53 (s, 3 H), 2.43 (s, 3 H), LCMS: 391.6 [M + H], HPLC purity: 98.99% |
| 6 | $^1$H-NMR (MeOD, 300 MHz): δ 8.78 (d, 2 H), 8.06 (d, 2 H), 7.23 (d, 1 H), 7.13 (d, 1 H), 7.06 (d, 1 H), 5.13 (s, 2 H), 3.89 (d, 6 H), 2.54 (s, 3 H), 2.42 (s, 3 H), LCMS: 391.4 [M + H], HPLC purity: 96.53% |
| 7 | $^1$H-NMR (MeOD, 300 MHz): δ 7.28 (s, 4 H), 7.22 (d, 1 H), 7.09 (d, 1 H), 7.04 (d, 1 7 H), 3.89 (d, 6 H), 3.84 (t, 2 H), 3.01 (t, 2 H), 2.49 (s, 3 H), 2.44 (s, 3 H), LCMS: 438.5 [M + H], HPLC purity: 99.45% |
| 8 | $^1$H-NMR (DMSO, 300 MHz): δ 7.39 (s, 4 H), 7.30 (d, 1 H), 7.17 (dd, 1 H), 7.04 (d, 1 H), 4.69 (d, 2 H), 3.79 (d, 6 H), 2.49 (s, 3 H), 2.38 (s, 3 H), LCMS: 424.7 [M + H], HPLC purity: 99.94% |
| 9 | $^1$H-NMR (MeOD, 300 MHz): δ 7.79 (d, 2 H), 7.63 (d, 2 H), 7.28 (d, 1 H), 7.15 (dd, 1 H), 7.96 (d, 1 H) 3.90 (d, 6 H), 2.57 (s, 3 H), 2.50 (s, 3 H), 2.15 (s, 3 H), LCMS: 433.6 [M + H], HPLC purity: 98.27% |
| 10 | $^1$H-NMR (MeOD, 300 MHz): δ 7.35 (d, 2 H), 7.23 (s, 1 H), 7.11 (m, 1 H), 7.05 (d, 1 H), 6.90 (d, 2 H), 4.75 (s, 2 H), 3.89 (d, 6 H), 3.78 (s, 2 H), 2.49 (d, 6 H), LCMS: 420.5 [M + H], HPLC purity: 99.64% |
| 11 | $^1$H-NMR (TFA, 300 MHz): δ 11.58, (s, 1 H), 8.25 (s, 1H), 8.03 (d, 1 H), 7.92 (d, 1 H), 7.74 (t, 1 H), 7.14 (d, 1 H), 6.98 (t, 2 H), 5.26 (s, 2 H), 4.01 (s, 3 H), 3.97 (s, 3 H), 3.30 (s, 3 H), 2.77 (s, 3 H), 2.51 (s, 3 H), LCMS: 468.3 [M + H], HPLC purity: 99.86% |
| 12 | $^1$H-NMR (DMSO, 300 MHz): δ 9.25, (t, 1 H), 8.15 (d, 2H), 7.38 (d, 1 H), 7.30 (d, 1 H), 7.17 (dd, 1 H), 7.02 (d, 1 H), 4.67 (d, 2 H), 3.78 (d, 6 H), 2.52 (s, 3 H), 2.37 (s, 3 H), LCMS: 407.8 [M + H], HPLC purity: 98.86% |
| 13 | $^1$H-NMR (DMSO, 300 MHz): δ 9.19, (t, 1 H), 8.20 (d, 2H), 7.76 (dd, 1 H), 7.29 (d, 1 H), 7.17 (dd, 1 H), 7.02 (d, 1 H), 6.78 (d, 1 H), 4.63 (d, 2 H), 3.92 (s, 3 H), 3.78, (s, 3 H), 2.41 (s, 3 H), LCMS: 421.7 [M + H], HPLC purity: 99.54% |
| 14 | $^1$H-NMR (DMSO, 300 MHz): δ 9.29, (t, 1 H), 7.78 (d, 2H), 7.54 (d, 2 H), 7.31 (s, 1 H), 7.29 (d, 2 H), 7.17 (dd, 1 H), 7.03 (d, 1 H), 4.78 (d, 2 H), 3.79 (d, 6 H), 2.53 (s, 3 H), 2.36 (s, 3 H), LCMS: 469.8 [M + H], HPLC purity: 98.53% |
| 15 | H-NMR (DMSO, 300 MHz): δ7.22 (s, 1 H), 7.09 (dd, 1 H), 7.03 (d, 1 H), 3.88 (d, 6 H), 3.48 (d, 2 H), 2.49 (s, 3 H), 2.44 (s, 3 H), 1.78 (m, 6 H), 1.28 (m, 4 H), 1.06 (m, 2 H), LCMS: 396.4 [M + H], HPLC purity: 99.77% |
| 16 | $^1$H-NMR (DMSO, 300 MHz): δ 9.12, (t, 1 H), 7.30 (d, 1H), 7.17 (dd, 1 H), 7.02 (d, 1 H), 6.97 (d, 1 H), 6.85 (s, 2 H), 5.97 (s, 2 H), 4.60 (d, 2 H), 3.78 (s, 6 H), 2.50 (s, 3 H), 2.39 (s, 3 H), LCMS: 434.0 [M + H], HPLC purity: 99.84% |
| 17 | $^1$H-NMR (MeOD, 300 MHz): δ 7.26, (d, 2 H), 7.22 (d, 1H), 7.10 (dd, 1 H), 7.03 (d, 1 H), 6.76 (d, 2 H), 4.71 (s, 2 H), 3.88 (s, 6 H), 2.47 (d, 6 H), LCMS: 406.4 [M + H], HPLC purity: 97.37% |
| 18 | $^1$H-NMR (CDCl$_3$, 300 MHz): δ 7.30 (d, 1 H), 7.17 (dd, 1 H), 6.96 (d, 1 H), 6.73 (br, 1 H), 4.18 (m, 1 H), 3.92 (m, 1 H), 3.94 (s, 3 H), 3.90 (s, 3 H), 3.86 (m, 1 H), 3.82 (m, 1 H), 3.61 (m, 1 H), 2.54 (d, 6 H), 2.08 (m, 1 H), 1.96 (m, 1 H), 1.68 (m, 1 H), LCMS: 384.1 [M + H], HPLC purity: 97.65% |
| 19 | $^1$H-NMR (MeOD, 300 MHz): δ 9.68 (s, 1 H), 9.16 (t, 1 H), 7.35 (d, 1H), 7.30 (d, 1 H), 7.16 (m, 3 H), 7.02 (d, 1 H), 4.66 (d, 2 H), 3.78 (s, 6 H), 2.67 (s, 3 H), 2.50 (s, 3 H), 2.32 (s, 3 H), LCMS: 483.1 [M + H], HPLC purity: 99.45% |
| 20 | $^1$H-NMR (DMSO, 300 MHz): δ 9.20 (t, 1 H), 7.37 (d, 2 H), 7.30 (m, 3 H), 7.25 (d, 1 H), 7.17 (d, 1 H), 7.02 (d, 1 H), 4.72 (d, 2 H), 3.78 (s, 6 H), 2.50 (s, 3 H), 2.38 (s, 3 H), LCMS: 390.1 [M + H], HPLC purity: 99.90% |
| 21 | $^1$H-NMR (DMSO, 300 MHz): δ 9.27 (t, 1 H), 7.39 (dd, 1 H), 7.30 (d, 1 H), 7.09 (d, 1 H), 7.02 (d, 1 H), 6.97 (d, 1 H), 4.84 (d, 2 H), 3.78 (d, 6 H), 2.50 (s, 3 H), 2.43 (s, 3 H), LCMS: 396.1 [M + H], HPLC purity: 99.96% |
| 22 | $^1$H-NMR (DMSO, 300 MHz): δ 9.26 (t, 1 H), 8.62 (d, 1 H), 8.47 (dd, 1 H), 7.80 (m, 1 H), 7.35 (dd, 1 H), 7.29 (d, 1 H), 7.17 (dd, 1 H), 7.02 (d, 1 H), 4.72 (d, 2 H), 3.78 (d, 6 H), 2.50 (s, 3 H), 2.39 (s, 3 H), LCMS: 391.1 [M + H], HPLC purity: 99.97% |
| 23 | $^1$H-NMR (DMSO, 300 MHz): δ 9.26 (bs, 1 H), 7.30 (d, 1 H), 7.17 (dd, 1 H), 7.02 (d, 1 H), 6.18 (d, 1 H), 5.99 (d, 1 H), 4.63 (d, 2 H), 3.78 (d, 6 H), 2.50 (s, 3 H), 2.40 (s, 3 H), 2.20 (s, 3 H), LCMS: 394.1 [M + H], HPLC purity: 99.61% |
| 24 | $^1$H-NMR (DMSO, 300 MHz): δ 12.01 (s, 1 H), 9.30 (t, 1 H), 7.85 (d, 2 H), 7.59 (d, 2 H), 7.30 (s, 1 H), 7.18 (d, 1 H), 7.03 (d, 1 H), 4.80 (d, 2 H), 3.98 (q, 2 H), 3.79 (d, 6 H), 2.52 (s, 3 H), 2.36 (s, 3 H), 1.10 (t, 3 H), LCMS: 541.0 [M + H], HPLC purity: 97.51% |

TABLE 3-continued

| Ex. | Analytical Data |
|---|---|
| 25 | $^1$H-NMR (DMSO, 300 MHz): δ 12.01 (s, 1 H), 9.29 (t, 1 H), 7.88 (d, 2 H), 7.58 (d, 2 H), 7.30 (s, 1 H), 7.18 (d, 1 H), 7.03 (d, 1 H), 4.80 (d, 2 H), 3.79 (d, 6 H), 2.52 (s, 3 H), 2.34 (s, 3 H), 2.18 (t, 2 H), 0.87 (t, 3 H), LCMS: 525.0 [M + H], HPLC purity: 99.96% |
| 26 | $^1$H-NMR (DMSO, 300 MHz): δ 9.30 (t, 1 H), 7.75 (d, 2 H), 7.57 (d, 2 H), 7.42 (dd, 1 H), 7.30 (s, 1 H), 7.18 (d, 1 H), 7.03 (d, 1 H), 4.80 (d, 2 H), 3.79 (d, 6 H), 2.52 (s, 3 H), 2.37 (s, 3 H), 2.33 (t, 2 H), LCMS: 483.2 [M + H], HPLC purity: 97.8% |
| 27 | $^1$H-NMR (DMSO, 300 MHz): δ 8.90 (t, 1 H), 7.57 (d, 1 H), 7.30 (d, 1 H), 7.18 (dd, 1 H), 7.02 (d, 1 H), 6.18 (d, 1 H), 4.65 (d, 2 H), 3.79 (d, 9 H), 2.52 (s, 3 H), 2.39 (s, 3 H), LCMS: 394.2 [M + H], HPLC purity: 99.0% |
| 28 | $^1$H-NMR (DMSO, 300 MHz): δ 8.16 (s, 1 H), 7.23 (d, 1 H), 7.13 (d, 1 H), 7.09 (dd, 1 H), 7.03 (d, 1 H), 4.91 (d, 2 H), 3.87 (d, 6 H), 2.49 (d, 6 H), LCMS: 381.2 [M + H], HPLC purity: 98.3% |
| 29 | $^1$H-NMR (MeOD, 300 MHz): δ 7.12 (d, 1 H), 7.01 (d, 2 H), 3.89 (d, 6 H), 3.74 (d, 2 H), 3.45 (d, 2 H), 3.04 (t, 2 H), 2.63 (s, 3 H), 2.45 (s, 3 H), 2.15 (b, 1 H), 2.05 (d, 2 H), 1.60 (b, 2 H), LCMS: 397.2 [M + H], HPLC purity: 99.9% |
| 30 | $^1$H-NMR (MeOH, 300 MHz): δ 8.79 (s, 2 H), 7.22 (d, 1 H), 7.10 (dd, 1 H), 7.03 (d, 1 H), 4.80 (s, 2 H), 3.87 (s, 6 H), 2.67 (s, 3 H), 2.49 (s, 3 H), 2.45 (s, 3 H), LCMS: 406.2 [M + H], HPLC purity: 99.4% |
| 31 | $^1$H-NMR (MeOD, 300 MHz): δ 9.28 (d, 1 H), 9.13 (dd, 1 H), 7.75 (d, 1 H), 7.23 (d, 1 H), 7.12 (dd, 1 H), 7.03 (d, 1 H), 4.91 (d, 2 H), 3.88 (s, 6 H), 2.51 (s, 3 H), 2.41 (s, 3 H), LCMS: 392.2 [M + H], HPLC purity: 98.8% |
| 32 | $^1$H-NMR (DMSO, 300 MHz): δ 9.22 (t, 1 H), 8.48 (d, 1 H), 7.67 (dd, 1 H), 7.29 (d, 1 H), 7.18 (dd, 1 H), 7.03 (d, 1 H), 4.66 (d, 2 H), 3.78 (s, 6 H), 2.42 (s, 3 H), 2.39 (s, 3 H), LCMS: 405.2 [M + H], HPLC purity: 99.9% |

BIOLOGICAL ASSAYS

Phosphatidyl Inositol Kinase Inhibition Assay

Inhibition of PI4 kinases was studied using the ADP-Glo™ Kinase Assay which is a luminescent kinase assay that measures ADP formed from a kinase reaction; ADP is converted into ATP, which is converted into light by Ultra-Glo™ Luciferase. The assay is performed in two steps; first, after the kinase reaction, an equal volume of ADP-Glo™ Reagent is added to terminate the kinase reaction and deplete the remaining ATP. In the second step, the Kinase Detection Reagent is added, which simultaneously converts ADP to ATP and allows the newly synthesized ATP to be measured using a coupled luciferase/luciferin reaction. The luminescent signal produced is proportional to the activity of the kinase.

Inhibition of PI3 kinases was studied using the HTRF (homogeneous time-resolved fluorescence) assay which is a universal method for identifying and characterizing the phosphotransferase activity induced by any ATP/ADP dependent target. The formation of ADP is detected by a specific monoclonal antibody labeled with $Eu^{3+}$ cryptate, and directly correlates with the amount of phosphorylated substrate in kinase assays Table 4 shows test results, expressed as $IC_{50}$ values (in μM) of some compounds of the invention vs. different kinases.

TABLE 4

| Kinase | Example 6 $IC_{50}$ (μM) | Example 14 $IC_{50}$ (μM) |
|---|---|---|
| PI4KIIIβ | 0.0013 | 0.0021 |
| PI4KIIIα | 3.2 | 1.3 |
| PI3Kβ | >10 | >10 |
| PI3Kα | 7.3 | >10 |

In Vitro Assay in Mammalian Cell Culture

The antiviral activity of compounds of the invention has been evaluated based on the ability of the compounds to prevent virus from causing viral cytopathic effects (CPE) in mammalian cell culture. Incubation time, cell line, cell density and virus titer differed from assay to assay but the general procedure was as follows: Cells were cultivated on 96 well flat bottom plates to approximately 90% confluence (20 000-90 000 cells/well) in a suitable media. The titer of the virus was determined by the standard method of tissue culture infective dose ($TCID_{50}$) on cells. Briefly, cells were infected with 50 μl of virus suspension, and diluted 10-fold in media. The plates were incubated in 37° C. with 5% $CO_2$ for 3-7 days and cells were inspected daily for CPE. After determining CPE, plates were stained with Gram's Crystal Violet solution and optical density was read at 540 nm. The highest virus dilution that resulted in >95% CPE was used in the assays. Substances at a final concentration of 2.5-20 μM and the virus were added to the cells and incubated for 3-7 days depending on the virus and cell line used. As controls, uninfected cells and cells infected with virus (no substance) were included on each plate. The cells were stained with crystal violet after determining the CPE on infected controls and the optical density was read at 540 nm. The inhibition capacity was calculated as a % by comparison with non-infected and infected controls.

Table 5 shows the inhibition capacity of compounds of the invention on different enteroviruses. + indicates $IC_{50}$<1 □M; ++ indicates $IC_{50}$<100 nM; +++ indicates $IC_{50}$<10 nM; EV6: Enterovirus 6; EV30: Enterovirus 30; EV68: Enterovirus 68; EV71: Enterovirus 71; B1: coxsackie B1 virus; B2: coxsackie B2 virus; B3: coxsackie B3 virus; B4: coxsackie B 4 virus; B5: coxsackie B5virus; Polio1: polio virus Sabin 1.

TABLE 5

| Ex. | EV6 | EV30 | EV68 | EV71 | B1 | B2 | B3 | B4 | B5 | Polio 1 |
|---|---|---|---|---|---|---|---|---|---|---|
| 1 | + | ++ | nd | +++ | ++ | +++ | + | nd | ++ | +++ |
| 2 | + | ++ | + | + | ++ | ++ | + | ++ | ++ | ++ |
| 3 | + | ++ | ++ | ++ | ++ | ++ | ++ | ++ | ++ | ++ |
| 4 | + | + | + | + | + | + | + | + | + | + |
| 5 | + | + | + | + | ++ | ++ | + | + | + | ++ |
| 6 | +++ | ++ | +++ | +++ | +++ | +++ | +++ | +++ | +++ | +++ |
| 7 | + | + | + | + | + | + | + | + | + | + |
| 8 | + | ++ | ++ | + | ++ | ++ | ++ | ++ | + | ++ |
| 9 | ++ | ++ | ++ | ++ | + | ++ | ++ | ++ | ++ | +++ |
| 10 | + | ++ | ++ | + | ++ | ++ | + | ++ | ++ | ++ |
| 11 | ++ | +++ | ++ | ++ | +++ | +++ | +++ | +++ | +++ | +++ |
| 12 | nd | + | + | + | + | + | + | + | + | + |
| 13 | nd | +++ | ++ | ++ | +++ | ++ | ++ | ++ | ++ | +++ |
| 14 | nd | +++ | +++ | +++ | ++ | ++ | ++ | ++ | +++ | +++ |
| 15 | + | + | + | + | + | + | + | + | + | + |
| 16 | + | ++ | ++ | ++ | ++ | ++ | ++ | +++ | ++ | ++ |
| 17 | ++ | ++ | ++ | +++ | +++ | +++ | ++ | ++ | +++ | +++ |
| 18 | + | + | + | + | + | + | + | + | + | + |
| 19 | + | ++ | ++ | +++ | ++ | ++ | ++ | +++ | + | ++ |
| 20 | ++ | ++ | ++ | ++ | ++ | ++ | ++ | +++ | ++ | ++ |
| 21 | ++ | ++ | ++ | ++ | +++ | +++ | ++ | ++ | ++ | ++ |
| 22 | ++ | ++ | ++ | ++ | ++ | ++ | ++ | ++ | ++ | ++ |
| 23 | ++ | ++ | ++ | ++ | +++ | ++ | ++ | +++ | ++ | +++ |
| 24 | − | − | + | + | − | + | − | + | − | + |
| 25 | − | − | + | − | − | − | − | − | − | − |
| 26 | + | + | − | + | + | ++ | + | ++ | + | ++ |
| 27 | + | ++ | +++ | ++ | +++ | +++ | ++ | +++ | ++ | +++ |
| 28 | ++ | +++ | − | ++ | ++ | ++ | ++ | ++ | + | ++ |
| 29 | − | − | − | − | − | − | − | − | − | − |
| 30 | + | ++ | ++ | ++ | + | + | + | ++ | + | ++ |
| 31 | + | − | ++ | ++ | + | + | + | +++ | + | + |
| 32 | ++ | +++ | ++ | ++ | ++ | ++ | +++ | ++ | ++ | ++ |

In Table 5 the signs have the following meaning:
+ IC$_{50}$ < 1 μM
++ IC$_{50}$ < 100 nM
+++ IC$_{50}$ < 10 nM
− Not determined or IC$_{50}$ > 1 μM

The invention claimed is:

1. A compound of formula (I)

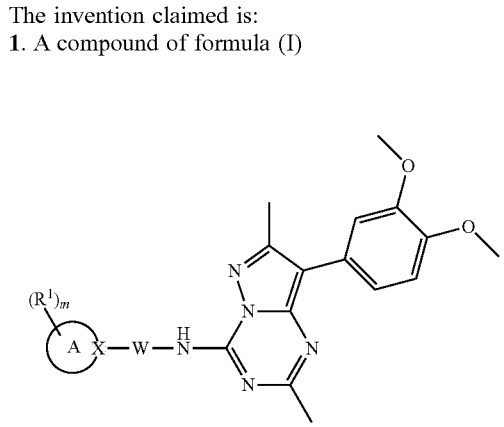

(I)

or a pharmaceutically acceptable salt thereof, wherein
W is CH$_2$ or CH$_2$—CH$_2$;
X is C;
ring A is phenyl or 5- or 6-membered heteroaryl;
m is an integer of from 0 to 3;
each R$^1$ is independently selected from C$_1$-C$_6$ alkyl optionally substituted by one or more halogen, R$^2$O, halogen, R$^3$R$^4$NC(O), R$^5$C(O)N(R$^6$), R$^7$OC(O), R$^8$C(O)O, R$^9$S(O)$_2$, R$^{10}$S(O)$_2$N(H), R$^{11}$C(O), R$^{12}$R$^{13}$N, $^-$O and R$^{14}$R$^{15}$NS(O)$_2$; and
when m is at least 2, two R$^1$ attached to adjacent atoms of ring A may form, together with the atoms to which they are attached, a 5- or 6-membered heterocyclic or carbocyclic ring;

each R$^2$, R$^3$, R$^4$, R$^5$, R$^6$, R$^7$, R$^8$, R$^9$, R$^{10}$, R$^{11}$, R$^{12}$, R$^{13}$ and R$^{14}$ is independently selected from H and C$_1$-C$_6$ alkyl, wherein any alkyl is optionally substituted by one or more halogen;
R$^{15}$ is selected from H, C$_1$-C$_6$ alkyl, R$^{16}$C(O), R$^{17}$OC(O), and R$^{18}$R$^{19}$NC(O); and
each R$^{16}$, R$^{17}$, R$^{18}$, and R$^{19}$ is independently selected from H and C$_1$-C$_6$ alkyl, wherein any alkyl is optionally substituted by one or more halogen.

2. The compound of claim 1, or a pharmaceutically acceptable salt thereof, wherein ring A is 5 or 6-membered heteroaryl.

3. The compound of claim 1, or a pharmaceutically acceptable salt thereof, wherein ring A is phenyl.

4. The compound of claim 1, or a pharmaceutically acceptable salt thereof, wherein ring A is 6-membered heteroaryl.

5. The compound of claim 1, or a pharmaceutically acceptable salt thereof, wherein W is CH$_2$.

6. The compound of claim 1, or a pharmaceutically acceptable salt thereof, wherein m is an integer of from 0 to 2.

7. The compound of claim 6, or a pharmaceutically acceptable salt thereof, wherein m is 1 or 2.

8. The compound of claim 6, or a pharmaceutically acceptable salt thereof, wherein W is CH$_2$.

9. A compound according to claim 1, selected from
8-(3,4-dimethoxyphenyl)-N-[(4-fluorophenyl)methyl]-2,7-dimethyl-pyrazolo[1,5-a][1,3,5]triazin-4-amine,
8-(3,4-dimethoxyphenyl)-2,7-dimethyl-N-[[4-(trifluoromethyl)phenyl]methyl]pyrazolo[1,5-a][1,3,5]triazin-4-amine, 8-(3,4-dimethoxyphenyl)-2,7-dimethyl-N-(p-tolylmethyl)pyrazolo[1,5-a][1,3,5]triazin-4-amine,
8-(3,4-dimethoxyphenyl)-N-[(4-isopropylphenyl)methyl]-2,7-dimethyl-pyrazolo[1,5-a][1,3,5]triazin-4-amine,
8-(3,4-dimethoxyphenyl)-2,7-dimethyl-N-(2-pyridylmethyl)pyrazolo[1,5-a][1,3,5]triazin-4-amine,
8-(3,4-dimethoxyphenyl)-2,7-dimethyl-N-(4-pyridylmethyl)pyrazolo[1,5-a][1,3,5]triazin-4-amine,
N-[2-(4-chlorophenyl)ethyl]-8-(3,4-dimethoxyphenyl)-2,7-dimethyl-pyrazolo[1,5-a][1,3,5]triazin-4-amine,
N-[(4-chlorophenyl)methyl]-8-(3,4-dimethoxyphenyl)-2,7-dimethyl-pyrazolo[1,5-a][1,3,5]triazin-4-amine,
N-[4-[[[8-(3,4-dimethoxyphenyl)-2,7-dimethyl-pyrazolo[1,5-a][1,3,5]triazin-4-yl]amino]methyl]phenyl]acetamide,
8-(3,4-dimethoxyphenyl)-N-[(4-methoxyphenyl)methyl]-2,7-dimethyl-pyrazolo[1,5-a][1,3,5]triazin-4-amine,
8-(3,4-dimethoxyphenyl)-2,7-dimethyl-N-[(3-methylsulfonylphenyl)methyl]pyrazolo[1,5-a][1,3,5]triazin-4-amine,
8-(3,4-dimethoxyphenyl)-2,7-dimethyl-N-[(1-oxidopyridin-1-ium-4-yl)methyl]pyrazolo[1,5-a][1,3,5]triazin-4-amine,
8-(3,4-dimethoxyphenyl)-N-[(6-methoxy-3-pyridyl)methyl]-2,7-dimethyl-pyrazolo[1,5-a][1,3,5]triazin-4-amine,
4-[[[8-(3,4-dimethoxyphenyl)-2,7-dimethyl-pyrazolo[1,5-a][1,3,5]triazin-4-yl]amino]methyl]benzenesulfonamide,
N-(1,3-benzodioxol-5-ylmethyl)-8-(3,4-dimethoxyphenyl)-2,7-dimethyl-pyrazolo[1,5-a][1,3,5]triazin-4-amine,
4-[[[8-(3,4-dimethoxyphenyl)-2,7-dimethyl-pyrazolo[1,5-a][1,3,5]triazin-4-yl]amino]methyl]phenol
N-[4-[[[8-(3,4-dimethoxyphenyl)-2,7-dimethyl-pyrazolo[1,5-a][1,3,5]triazin-4-yl]amino]methyl]phenyl]methanesulfonamide,
N-benzyl-8-(3,4-dimethoxyphenyl)-2,7-dimethyl-pyrazolo[1,5-a][1,3,5]triazin-4-amine,
8-(3,4-dimethoxyphenyl)-2,7-dimethyl-N-(2-thienylmethyl)pyrazolo[1,5-a][1,3,5]triazin-4-amine,
8-(3,4-dimethoxyphenyl)-2,7-dimethyl-N-(3-pyridylmethyl)pyrazolo[1,5-a][1,3,5]triazin-4-amine,
8-(3,4-dimethoxyphenyl)-2,7-dimethyl-N-[(5-methyl-2-furyl)methyl]pyrazolo[1,5-a][1,3,5]triazin-4-amine,
methyl N-[4-[[[8-(3,4-dimethoxyphenyl)-2,7-dimethyl-pyrazolo[1,5-a][1,3,5]triazin-4-yl]amino]methyl]phenyl]sulfonylcarbamate,
N-[4-[[[8-(3,4-dimethoxyphenyl)-2,7-dimethyl-pyrazolo[1,5-a][1,3,5]triazin-4-yl]amino]methyl]phenyl]sulfonylpropanamide,
N-methyl-4-[[[8-(3,4-dimethoxyphenyl)-2,7-dimethyl-pyrazolo[1,5-a][1,3,5]triazin-4-yl]amino]methyl]benzenesulfonamide,
8-(3,4-dimethoxyphenyl)-2,7-dimethyl-N-[(1-methyl-1H-pyrazol-3-yl)methyl]pyrazolo[1,5-a][1,3,5]triazin-4-amine,
8-(3,4-dimethoxyphenyl)-2,7-dimethyl-N-[(1,3-oxazol-5-yl)methyl]pyrazolo[1,5-a][1,3,5]triazin-4-amine,
8-(3,4-dimethoxyphenyl)-2,7-dimethyl-N-[(2-methylpyrimidin-5-yl)methyl]pyrazolo[1,5-a][1,3,5]triazin-4-amine,
8-(3,4-dimethoxyphenyl)-2,7-dimethyl-N-[(pyridazin-4-yl)methyl]pyrazolo[1,5-a][1,3,5]triazin-4-amine, and
8-(3,4-dimethoxyphenyl)-2,7-dimethyl-N-[(6-methyl-pyridin-3-yl)methyl]pyrazolo[1,5-a][1,3,5]triazin-4-amine,
or a pharmaceutically acceptable salt thereof.

10. A pharmaceutical composition comprising a compound according to claim 1 and optionally a pharmaceutically acceptable excipient.

11. A method of treatment of a viral infection by administering a compound according to claim 1 to a mammal in need thereof.

12. The compound of claim 2, or a pharmaceutically acceptable salt thereof, wherein W is $CH_2$.

13. The compound of claim 3, or a pharmaceutically acceptable salt thereof, wherein W is $CH_2$.

14. The compound of claim 4, or a pharmaceutically acceptable salt thereof, wherein W is $CH_2$.

15. The compound of claim 1, having the formula (Ie)

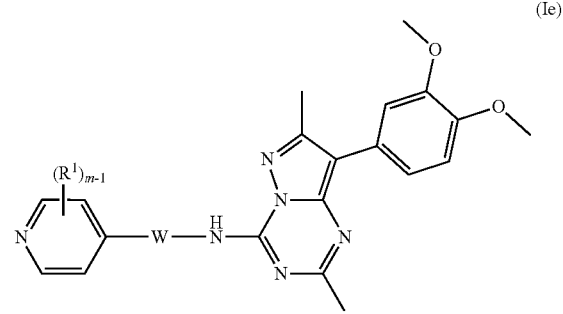

or a pharmaceutically acceptable salt thereof,
wherein $R^1$ and W are as defined in claim 1; and m is 1, 2, or 3.

16. The compound of claim 15, wherein m is 1 or 2.

17. The compound of claim 15, wherein W is $CH_2$.

* * * * *